US009612243B1

(12) United States Patent
Morre

(10) Patent No.: US 9,612,243 B1
(45) Date of Patent: Apr. 4, 2017

(54) METHODS AND COMPOSITIONS FOR TARGETED TWO-DIMENSIONAL WESTERN BLOT ANALYSIS FOR EARLY CANCER DETECTION AND CANCER DIAGNOSIS UP TO TEN YEARS IN ADVANCE OF CLINICAL SYMPTOMS OF MALIGNANT DISEASE

(71) Applicant: Mor-NuCo Enterprises, Inc., West Lafayette, IN (US)

(72) Inventor: D. James Morre, West Lafayette, IN (US)

(73) Assignee: MOR-NUCO ENTERPRISES, INC., West Lafayette, IN (US)

( * ) Notice: Subject to any disclaimer, the term of this patent is extended or adjusted under 35 U.S.C. 154(b) by 0 days.

(21) Appl. No.: 15/169,205

(22) Filed: May 31, 2016

(51) Int. Cl.
G01N 33/574 (2006.01)

(52) U.S. Cl.
CPC ... *G01N 33/57488* (2013.01); *G01N 2333/47* (2013.01)

(58) Field of Classification Search
None
See application file for complete search history.

(56) References Cited

U.S. PATENT DOCUMENTS

| 7,053,188 | B2 | 5/2006 | Morre et al. |
| 9,283,257 | B2 | 3/2016 | Morre |
| 9,459,256 | B2 | 10/2016 | Morre et al. |
| 2003/0207340 | A1 | 11/2003 | Morre et al. |
| 2009/0042209 | A1 | 2/2009 | Hostetler |
| 2014/0212896 | A1* | 7/2014 | Morre ............. G01N 33/57419 435/7.23 |

FOREIGN PATENT DOCUMENTS

| WO | 2011109663 A1 | 9/2011 |
| WO | 2013052926 A2 | 4/2013 |

OTHER PUBLICATIONS

Morre et al. in "Ecto-Nox Proteins Chapter 12 Cancer Diagnostic Applications of ENOX2 Protein" by Springer NY, 2013, p. 419-434.*
Bruno, et al. "Stimulation of NADH oxidase activity from rat liver plasma membranes by growth factors and hormones is decreased or absent with hepatoma plasma membranes" Biochem J. (1992) 284, 625-628.
Cho, et al. "Monoclonal antibody to a cancer-specific and drug-responsive hydroquinone (NADH) oxidase from the sera of cancer patients" Cancer Immunol Immunother (2002) 51:121-129.
Chueh, et al. "Molecular Cloning and Characterization of a Tumor-Associated, Growth-Related, and Time-Keeping Hydroquinone (NADH) Oxidase (tNOX) of the HeLa Cell Surface" Biochemistry 2002, 41, 3732-3741.

Del Castillo-Olivares, et al. "A Drug-Responsive and Protease-Resistant Peripheral NADH Oxidase Complex from the Surface of HeLa S Cells" Archives of Biochemistry and Biophysics, vol. 358, No. 1, Oct. 1, 1998, pp. 125-140.
Morre, D. James "NADH oxidase activity of HeLa plasma membranes inhibited by the antitumor sulfonylurea N-(4-methylphenylsulfonyl)-N'-(4-chlorphenyl) urea (LY181984) at an external site" Biochiimica et Biophysica Acta 1240 (1995) 201-208.
Morre, et al. "Capsaicin inhibits preferentially the NADH oxidase and growth of transformed cells in culture" Proc. Natl. Acad. Sci. USA, vol. 92, pp. 1831-1835, Mar. 1995, Cell Biology.
Morre, et al. "A Circulating Form of NADH Oxidase Activity Responsive to the Antitumor Sulfonylurea N-4-(methylphenysulfonyl)-N'-(4-Chlorophenyl)urea (LY181984) Specific to Sera from Cancer Patients" Journal of Bioenergetics and Biomembranes, vol. 29, No. 3, 1997.
Morre, et al. "NADH Oxidase Activity from Sera Altered by Capsaicin is Widely Distributed among Cancer Patients" Archives of Biochemistry and Biophysics, vol. 342, No. 2, Jun. 15, 1997, pp. 224-230.
Morre, D. James "Plasma Membrane Redox Systems and Their Role in Biological Stress and Disease" NADH Oxidase: A Multifunctional Ectoprotein of the Eukaryotic Cell Surface, 1998 (Asard, H., Berczi, A. and Caubergs, R. J., (Eds) pp. 121-156.
Morre, et al. "Surface NADH Oxidase of HeLa Cells Lacks Intrinsic Membrane Binding Motifs" Archives of Biochemistry and Biophysics, vol. 392, No. 2, Aug. 15, 2001, pp. 251-256.
Morre, et al. "Cell Surface NADH Oxidases (ECTO-NOX Proteins) with Roles in Cancer, Cellular Time-keeping, Growth, Aging and Neurodegenerative Diseases" Free Radical Research, vol. 37, No. 8 (Aug. 2003), pp. 795-808.
Bird, et al. "Single-chain antigen-binding proteins." Science, Oct. 21, 1988, vol. 242, No. 4877, pp. 423-426.
Braman, et al., "Site-Directed Mutagenesis Using Double-Stranded Plasmid DNA Templates," Chapter 3 of Methods in Molecular Biology, vol. 57, In Vitro Mutagenesis Protocols, 1996, pp. 31-44.
Chomczynski, et al. "Single-step method of RNA isolation by acid guanidinium thiocyanate-phenol-chloroform extraction" (1987) Anal. Biochem. 162:156-159.
Daugherty, et al. "Polymerase chain reaction facilitates the cloning, CDRgrafting, and rapid expression of a murine monoclonal antibody directed against the CD18 component of leukocyte integrins" 1991. Nucleic Acids Research 19:2471-2476.

(Continued)

*Primary Examiner* — Jacob Cheu
(74) *Attorney, Agent, or Firm* — Edwin S. Flores; Chalker Flores, LLP

(57) ABSTRACT

The present invention includes methods for detecting benign to malignant transformation of a cancer in a subject, comprising the steps of: collecting a sample from the subject prior to electrophoretic protein separation; activating electrophoretically separated ENOX2 transcript variants with an ENOX2 electron donor; and detecting the presence of the one or more activated ENOX2 transcript variants using a pan-ENOX2 detectable binding reagent, wherein the presence of one or more activated ENOX2 transcript variants in the sample is indicative of the malignant transformation of the cancer, whereby a 10 to 100 fold increase in detection sensitivity is obtained for the one or more activated ENOX2 transcript variants when compared to an equivalent non-activated ENOX2 transcript variant.

28 Claims, 11 Drawing Sheets

(56) References Cited

OTHER PUBLICATIONS

Davis, et al. "Single Chain Antibody (SCA) Encoding Genes: One-Step Construction and Expression in Eukaryotic Cells" (1991) Bio/Technology 9:165-169.
Davies, et al., "Spotlight on tNOX: A tumor-selective target for cancer therapies" 2005. Drug News Perspect 19: 223-225.
GenBank Accession No. AF207881, 2002 publication year.
Glockshuber, et al. "A comparison of strategies to stabilize immunoglobulin Fv fragments" 1990. Biochemistry 29:1262-1367.
Goncalves, et al., "Clinical Application of Proteomics in Breast Cancer: State of the Art and Perspectives" Medical Principles and Practice, vol. 20, No. 1, 2011, pp. 4-18.
Gough, NM "Rapid and quantitative preparation of cytoplasmic RNA from small numbers of cells" (1988) Anal. Biochem 173:93-95.
Hostetler, et al. "Cancer Site-Specific Isoforms of ENOX2 (tNOX), A Cancer-Specific Cell Surface Oxidase" 2009 (Clin. Proteomics 5: 46-51).
Howlander, et al. SEER Cancer Statistics Review, 1975-2012, National Cancer Institute, Bethesda, Md, 2014 publication year.
Huston, et al. "Protein Engineering of Antibody Binding Sites: Recovery of Specific Activity in an Anti-Digoxin Single-Chain Fv Analogue Produced in *Escherichia coli*" 1988. Proc. Natl. Acad. Sci. USA 85:5879-5883.
Jiang, Z., et al., "Molecular Cloning and Characterization of a Candidate Human Growth-Related and Time-Keeping Constitutive Cell Surface Hydroquinone (NADH) Oxidase," Biochemistry, vol. 47, No. 52, Sep. 2008, pp. 14028-14038.
Jones, et al. "Rapid PCR-Cloning of Full-Length Mouse Immunoglobulin Variable Regions" 1991. Bio/Technology 9:88-89.
Korean Intellectual Property Office, International Search Report and Written Opinion for PCT/US2012/059141 dated Mar. 25, 2013, 14 pp.
Lee et al., "Effect of BRCA1/2 mutation on short-term and long-term breast cancer survival: a systematic review and meta-analysis." Breast Cancer Research and Treatment, Jul. 2010, vol. 122, Issue 1, pp. 11-25.
Morre, et al. (1988) "Inhibition of Plasma membrane redox activities and elongation of growth of soybean," Phsiologia Plantarum, vol. 72, 1988, pp. 236-240.
Morre (1995) "The antitumor sulfonylurea N-4-methylphenylsulfonylurea-N'-chlorophenylurea LY181984 inhibits NADH oxidase activity of HeLa plasma membranes" Biochim. Biophys. Acta 1240: 201-208.

Morre, D.J., et al. (1999) "Use of dipyridyl-dithio substrates to measure directly the protein disulfide-thiol interchange activity of the auxin stimulated NADH: Protein disulfide reductase (NADH oxidase) of soybean plasma membranes," Molecular and Cellular Biochemistry, vol. 200, Dec. 15, 1998, pp. 7-13.
Morre, D.J., et al (1999) "Glaucarubolone and Simalikalactone D, Respectively, Preferentially Inhibit Auxin-Induced and Constitutie Components of Plant Cell Enlargement and the Plasma Membrane NADH Oxidase," Int. J. Plant Sci., 160(2), pp. 291-297.
Morre, et al., "Cancer Type-Specific tNOX Isoform: A Putative Family of Redox Protein Splice Variants with Cancer Diagnostics and Prognostic Potential" Biofactors, vol. 34, (2008) No. 3, pp. 201-207.
Morre, et al., "Early Detection: An Opportunity for Cancer Prevention Through Early Intervention" Cancer Prevention—from Mechanisms to Translational Benefits, Apr. 20, 2012, pp. 389-402.
Morre, et al., "The Auxin-Stimulated ENOX and Auxin Stimulation of Plant Growth," Chapter 10 of Ecto-Nox Proteins: Growth, Cancer; Aging, Springer Science+Business Media New York 2013, pp. 313-342.
Smith, PK, et al., "Measurement of protein using bicinchoninic acid," Anal. Biochem., May 15, 1987, vol. 163:1: 279.
Tang, et al. "Alternative splicing as the basis for specific localization of tNOX, a unique hydroquinone (NADH) oxidase, to the cancer cell surface" 2007. Biochemistry 46:12337-12346; 2008.
Tang, et al., "Molecular Cloning and characterization of human age-related NADH oxidase (arNOX) proteins as members of the TM9 suprefamily of transmembrane proteins," Advances in Biological Chemistry, Apr. 2013, vol. 3, pp. 187-197.
Wang. et al., "NADH oxidase activity (NOX) and enlargement of HeLa cells oscillate with two dijerent temperature-compensated period lengths of 22 and 24 minutes corresponding to dijerent NOX forms" 2001. Biochim. Biophys. Acta 1539:192-204.
Weinberg, 2007. The Biology of Cancer, Garland Science.
Wu, et al., "Next-Generation Sequencing of MicroRNAs for Breast Cancer Detection." Journal of Biomedicine and Biotechnology, Mar. 24, 2011, vol. 2011, pp. 597-145.
Extended European Search Report of 16180364.8 dated Nov. 11, 2016, 12 pp.
Hoopes, et al., "Staining Electrophoretic Gels for Laccase and Peroxidase Activity Using 1,8-Diaminonaphthalene," Analyt. Biochem., 293 (1), May 1, 2001, pp. 96-101.
Morre, et al., "ENOX2-based early detection (ONCOblot) of asbestos-induced malignant mesothelioma 4-10 years in advance of clinical symptoms," Clin. Proteomics, 13:2, Jan. 22, 2016; 8 pp.
Sock, J., et al., "Activity Staining of Blotted Enzymes by Reaction Coupling with Transfer Membrane-Immobilized Auxiliary Enzymes," Analyt. Biochem., 171 (2), Nov. 16, 1987, pp. 310-319.

* cited by examiner

FIG. 8A    FIG. 8B    FIG. 8C    FIG. 8D    FIG. 8E
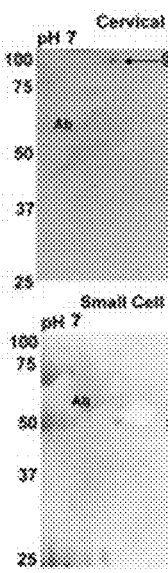 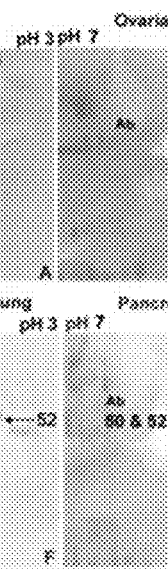 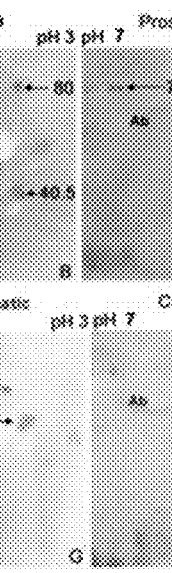 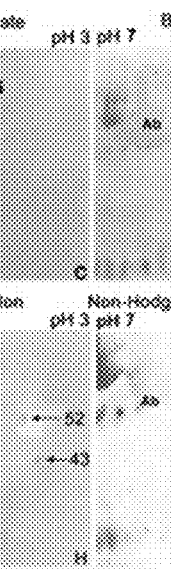 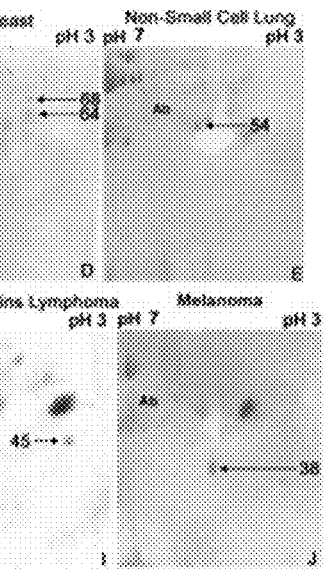
FIG. 8F    FIG. 8G    FIG. 8H    FIG. 8I    FIG. 8J
FIGS. 8A – 8J
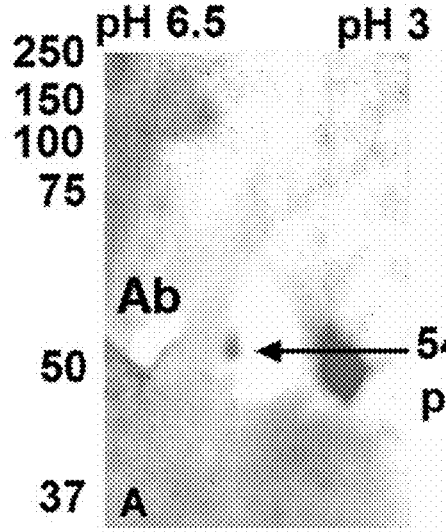 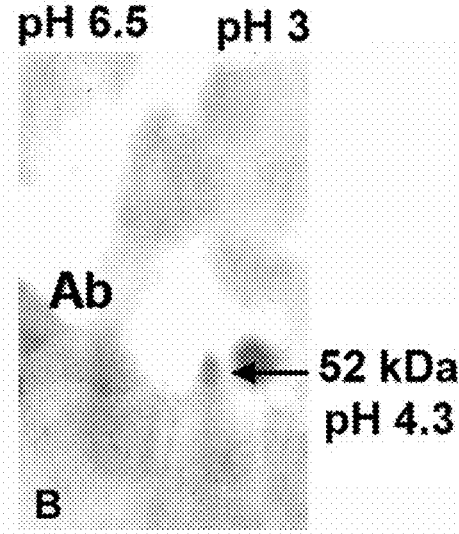
FIG. 9A    FIG. 9B

SEQUENCE LISTING

<160> NUMBER OF SEQ ID NOS: 25

<210> SEQ ID NO 1
<211> LENGTH: 16
<212> TYPE: PRT
<213> ORGANISM: Homo sapiens

<400> SEQUENCE: 1

Glu Glu Met Thr Glu Thr Lys Glu Thr Glu Glu Ser Ala Leu Val Ser
1               5                   10                  15

<210> SEQ ID NO 2
<211> LENGTH: 16
<212> TYPE: PRT
<213> ORGANISM: Homo sapiens

<400> SEQUENCE: 2

Gly Thr Asp Cys Val Ala Lys Glu Ala Thr Glu Ala Ala Lys Cys Asn
1               5                   10                  15

<210> SEQ ID NO 3
<211> LENGTH: 16
<212> TYPE: PRT
<213> ORGANISM: Homo sapiens

<400> SEQUENCE: 3

Cys Leu Asp Gly Thr Arg Lys Pro Val Glu Glu Tyr Ala Asn Cys His
1               5                   10                  15

<210> SEQ ID NO 4
<211> LENGTH: 45
<212> TYPE: DNA
<213> ORGANISM: Homo sapiens

<400> SEQUENCE: 4 ggcggggtg gtagctgcgg cggtggatcg tgtggcggtg gcagt                45

<210> SEQ ID NO 5
<211> LENGTH: 15
<212> TYPE: PRT
<213> ORGANISM: Homo sapiens

<400> SEQUENCE: 5

Gly Gly Gly Gly Ser Cys Gly Gly Gly Ser Cys Gly Gly Gly Ser
1               5                   10                  15

<210> SEQ ID NO 6
<211> LENGTH: 690
<212> TYPE: DNA
<213> ORGANISM: Homo sapiens

<400> SEQUENCE: 6
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gatttcttta gcaagctacc tgaaatgctg aaaatgttcg aagatcgttt atgtcataaa     420
acatatttaa atggtgatca tgtaacccat cctgacttca tgttgtatga cgctcttgat     480

```
gttgttttat acatggaccc aatgtgcctg gatgcgttcc caaaattagt ttgttttaaa    540
aaacgtattg aagctatccc acaaattgat aagtacttga atccagcaa gtatatagca     600 tggcctttgc agggctggca agccacgttt ggtggtggcg accatcctcc aaaatcggat    660
ctggttccgc gtggatcccc aggaattccc                                     690
```

<210> SEQ ID NO 7
<211> LENGTH: 357
<212> TYPE: DNA
<213> ORGANISM: Homo sapiens

<400> SEQUENCE: 7

```
gaggtcaagc tgcaggagtc aggaactgaa gtggtaaagc ctggggcttc agtgaagttg     60
tcctgcaagg cttctggcta catcttcaca agttatgata tagactgggt gaggcagacg    120
cctgaacagg gacttgagtg gattggatgg attttttcctg agagggggag tactgaatac   180
aatgagaagt tcaagggcag ggccacactg agtgtagaca gtcctccag cacagcctat     240 atggagctca ctaggctgac atctgaggac tctgctgtct atttctgtgc tagaggggac    300
tactataggc gctactttga cttgtgggc caagggacca cggtcaccgt ctcctca        357
```

<210> SEQ ID NO 8
<211> LENGTH: 321
<212> TYPE: DNA
<213> ORGANISM: Homo sapiens

<400> SEQUENCE: 8

```
gaaaatgtgc tcacccagtc tccagcaatc atgtctgcat ctccagggga gagggtcacc     60
atgacctgca gtgccagctc aagtatacgt tacatatatt ggtaccaaca gaagcctgga    120
tcctccccca gactcctgat ttatgacaca tccaacgtgg ctcctggagt cccttttcgc    180
ttcagtggca gtgggtctgg gacctcttat tctctcacaa tcaaccgaat ggaggctgag    240
gatgctgcca cttattactg ccaggagtgg agtggttatc cgtacacgtt cggagggggg    300
accaagctgg agctgaaagc g                                              321
```

<210> SEQ ID NO 9
<211> LENGTH: 1413
<212> TYPE: DNA
<213> ORGANISM: Homo sapiens

<400> SEQUENCE: 9

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg agtttcccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acgtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca     600 tggcctttgc agggctggca agccacgttt ggtggtggcg accatcctcc aaaatcggat    660
```

| | |
|---|---|
| ctggttccgc gtggatcccc aggaattccc gaggtcaagc tgcaggagtc aggaactgaa | 720 |
| gtggtaaagc ctggggcttc agtgaagttg tcctgcaagg cttctggcta catcttcaca | 780 |
| agttatgata tagactgggt gaggcagacg cctgaacagg acttgagtg gattggatgg | 840 |
| attttcctg gagaggggag tactgaatac aatgagaagt tcaagggcag ggccacactg | 900 |
| agtgtagaca agtcctccag cacagcctat atggagctca ctaggctgac atctgaggac | 960 |
| tctgctgtct atttctgtgc tagaggggac tactataggc gctactttga cttgtggggc | 1020 |
| caagggacca cggtcaccgt ctcctcaggc gggggtggta gctgcggcgg tggatcgtgt | 1080 |
| ggcggtggca gtgaaaatgt gctcacccag tctccagcaa tcatgtctgc atctccaggg | 1140 |
| gagagggtca ccatgacctg cagtgccagc tcaagtatac gttacatata ttggtaccaa | 1200 |
| cagaagcctg gatcctcccc cagactcctg atttatgaca catccaacgt ggctcctgga | 1260 |
| gtcccttttc gcttcagtgg cagtgggtct gggacctctt attctctcac aatcaaccga | 1320 |
| atggaggctg aggatgctgc cacttattac tgccaggagt ggagtggtta ccgtacacg | 1380 |
| ttcggagggg ggaccaagct ggagctgaaa gcg | 1413 |

<210> SEQ ID NO 10
<211> LENGTH: 1413
<212> TYPE: DNA
<213> ORGANISM: Homo sapiens

<400> SEQUENCE: 10

| | |
|---|---|
| atgtcccta tactaggtta ttggaaaatt aagggccttg tgcaacccac tcgacttctt | 60 |
| ttggaatatc ttgaagaaaa atatgaagag catttgtatg agcgcgatga aggtgataaa | 120 |
| tggcgaaaca aaaagtttga attgggtttg agtttccca atcttcctta ttatattgat | 180 |
| ggtgatgtta aattaacaca gtctatggcc atcatacgtt atatagctga caagcacaac | 240 |
| atgttgggtg gttgtccaaa agagcgtgca gagatttcaa tgcttgaagg agcggttttg | 300 |
| gatattgat acgtgtttc gagaattgca tatagtaaag actttgaaac tctcaaagtt | 360 |
| gattttctta gcaagctacc tgaaatgctg aaaatgttcg aagatcgttt atgtcataaa | 420 |
| acatatttaa atggtgatca tgtaacccat cctgacttca tgttgtatga cgctcttgat | 480 |
| gttgttttat acatggaccc aatgtgcctg gatgcgttcc caaaattagt ttgttttaaa | 540 |
| aaacgtattg aagctatccc acaaattgat aagtacttga atccagcaa gtatatagca | 600 |
| tggccttgc agggctggca agccacgttt ggtggtggcg accatcctcc aaaatcggat | 660 |
| ctggttccgc gtggatcccc aggaattccc gaggtcaagc tgcaggagtc aggaactgaa | 720 |
| gtggtaaagc ctggggcttc agtgaagttg tcctgcaagg cttctggcta catcttcaca | 780 |
| agttatgata tagactgggt gaggcagacg cctgaacagg acttgagtg gattggatgg | 840 |
| attttcctg gagaggggag tactgaatac aatgagaagt tcaagggcag ggccacactg | 900 |
| agtgtagaca agtcctccag cacagcctat atggagctca ctaggctgac atctgaggac | 960 |
| tctgctgtct atttctgtgc tagaggggac tactataggc gctactttga cttgtggggc | 1020 |
| caagggacca cggtcaccgt ctcctcaggc gggggtggta gctgcggcgg tggatcgtgt | 1080 |
| ggcggtggca gtgaaaatgt gctcacccag tctccagcaa tcatgtctgc atctccaggg | 1140 |
| gagagggtca ccatgacctg cagtgccagc tcaagtatac gttacatata ttggtaccaa | 1200 |
| cagaagcctg gatcctcccc cagactcctg atttatgaca catccaacgt ggctcctgga | 1260 |
| gtcccttttc gcttcagtgg cagtgggtct gggacctctt attctctcac aatcaaccga | 1320 |
| atggaggctg aggatgctgc cacttattac tgccaggagt ggagtggtta ccgtacacg | 1380 | ttcggagggg ggaccaagct ggagctgaaa gcg                                    1413

<210> SEQ ID NO 11
<211> LENGTH: 471
<212> TYPE: PRT
<213> ORGANISM: Homo sapiens

<400> SEQUENCE: 11

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Glu Val Lys Leu Gln Glu Ser Gly Thr Glu
225                 230                 235                 240

Val Val Lys Pro Gly Ala Ser Val Lys Leu Ser Cys Lys Ala Ser Gly
                245                 250                 255

Tyr Ile Phe Thr Ser Tyr Asp Ile Asp Trp Val Arg Gln Thr Pro Glu
            260                 265                 270

Gln Gly Leu Glu Trp Ile Gly Trp Ile Phe Pro Gly Glu Gly Ser Thr
        275                 280                 285

Glu Tyr Asn Glu Lys Phe Lys Gly Arg Ala Thr Leu Ser Val Asp Lys
    290                 295                 300

Ser Ser Ser Thr Ala Tyr Met Glu Leu Thr Arg Leu Thr Ser Glu Asp
305                 310                 315                 320

Ser Ala Val Tyr Phe Cys Ala Arg Gly Asp Tyr Tyr Arg Arg Tyr Phe
                325                 330                 335

Asp Leu Trp Gly Gln Gly Thr Thr Val Thr Val Ser Ser Gly Gly Gly
            340                 345                 350

Gly Ser Cys Gly Gly Gly Ser Cys Gly Gly Gly Ser Glu Asn Val Leu
        355                 360                 365

```
Thr Gln Ser Pro Ala Ile Met Ser Ala Ser Pro Gly Glu Arg Val Thr
    370                 375                 380

Met Thr Cys Ser Ala Ser Ser Ile Arg Tyr Ile Tyr Trp Tyr Gln
385                 390                 395                 400

Gln Lys Pro Gly Ser Ser Pro Arg Leu Leu Ile Tyr Asp Thr Ser Asn
                405                 410                 415

Val Ala Pro Gly Val Pro Phe Arg Phe Ser Gly Ser Gly Ser Gly Thr
                420                 425                 430

Ser Tyr Ser Leu Thr Ile Asn Arg Met Glu Ala Glu Asp Ala Ala Thr
        435                 440                 445

Tyr Tyr Cys Gln Glu Trp Ser Gly Tyr Pro Tyr Thr Phe Gly Gly Gly
    450                 455                 460

Thr Lys Leu Glu Leu Lys Ala
465                 470

<210> SEQ ID NO 12
<211> LENGTH: 42
<212> TYPE: DNA
<213> ORGANISM: Homo sapiens

<400> SEQUENCE: 12
ggatccccag gaattcccga ggtcaagctg caggagtcag ga                               42

<210> SEQ ID NO 13
<211> LENGTH: 8
<212> TYPE: PRT
<213> ORGANISM: Homo sapiens

<400> SEQUENCE: 13

Gly Thr Thr Val Thr Val Ser Ser
1               5

<210> SEQ ID NO 14
<211> LENGTH: 15
<212> TYPE: PRT
<213> ORGANISM: Homo sapiens

<400> SEQUENCE: 14

Gly Gly Gly Gly Ser Cys Gly Gly Ser Cys Gly Gly Gly Ser
1               5                   10                  15

<210> SEQ ID NO 15
<211> LENGTH: 69
<212> TYPE: DNA
<213> ORGANISM: Homo sapiens

<400> SEQUENCE: 15
gggaccacgg tcaccgtctc ctcaggcggg ggtggtagct gcggcggtgg atcgtgtggc           60
ggtggcagt                                                                   69

<210> SEQ ID NO 16
<211> LENGTH: 23
<212> TYPE: PRT
<213> ORGANISM: Homo sapiens

<400> SEQUENCE: 16

Gly Thr Thr Val Thr Val Ser Ser Gly Gly Gly Gly Ser Cys Gly
1               5                   10                  15

Gly Ser Cys Gly Gly Gly Ser
                20
```

```
<210> SEQ ID NO 17
<211> LENGTH: 63
<212> TYPE: DNA
<213> ORGANISM: Homo sapiens

<400> SEQUENCE: 17
accgccacac gatccaccgc cgcagctacc accccgcct gaggagacgg tgaccgtggt    60
ccc                                                                 63

<210> SEQ ID NO 18
<211> LENGTH: 21
<212> TYPE: PRT
<213> ORGANISM: Homo sapiens

<400> SEQUENCE: 18

Gly Gly Ser Cys Gly Gly Gly Ser Cys Gly Gly Gly Ser Glu Asn Val
1               5                   10                  15

Leu Thr Gln Ser Pro
            20

<210> SEQ ID NO 19
<211> LENGTH: 63
<212> TYPE: DNA
<213> ORGANISM: Homo sapiens

<400> SEQUENCE: 19
ggtggtagct gcggcggtgg atcgtgtggc ggtggcagtg aaaatgtgct cacccagtct    60
cca                                                                 63

<210> SEQ ID NO 20
<211> LENGTH: 21
<212> TYPE: PRT
<213> ORGANISM: Homo sapiens

<400> SEQUENCE: 20

Gly Gly Ser Cys Gly Gly Gly Ser Cys Gly Gly Gly Ser Glu Asn Val
1               5                   10                  15

Leu Thr Gln Ser Pro
            20

<210> SEQ ID NO 21
<211> LENGTH: 63
<212> TYPE: DNA
<213> ORGANISM: Homo sapiens

<400> SEQUENCE: 21
ggtggtagct gcggcggtgg atcgtgtggc ggtggcagtg aaaatgtgct cacccagtct    60
cca                                                                 63

<210> SEQ ID NO 22
<211> LENGTH: 39
<212> TYPE: DNA
<213> ORGANISM: Homo sapiens

<400> SEQUENCE: 22
gaacgccagc acatggacag ctgactcgag cggccggtg                          39

<210> SEQ ID NO 23
<211> LENGTH: 39
<212> TYPE: DNA
```

<213> ORGANISM: Homo sapiens

<400> SEQUENCE: 23

| caccggccgc tcgagtcagc tgtccatgtg ctggcgttc | 39 |

<210> SEQ ID NO 24
<211> LENGTH: 1464
<212> TYPE: DNA
<213> ORGANISM: Homo sapiens

<400> SEQUENCE: 24

| aaaaaacaat gcaaagtggt aaaagcctgg ggcttcagtg aagttgtcct gcaaggcttc | 60 |
| tggctacatc ttcacaagtt atgatataga ctgggtgagg cagacgcctg aacagggact | 120 |
| tgagtggatt ggatggattt ttcctggaga ggggagtact gaatacaatg agaagttcaa | 180 |
| gggcagggcc acactgagtg tagacaagtc ctccagcaca gcctatatgg agctcactag | 240 |
| gctgacatct gaggactctg ctgtctattt ctgtgctaga ggggactact acaggcgcta | 300 |
| cttggacttg tggggccaag gaccacggt caccgtctcc tcaggcgggg gtggtagctg | 360 |
| cggcggtgga tcgtgtggcg gtggcagtga aaatgtgctc acccagtctc cagcaatcat | 420 |
| gtctgcatct ccaggggaga gggtcaccat gacctgcagt gccagctcaa gtatacgtta | 480 |
| catatattgg taccaacaga agcctggatc ctcccccaga ctcctgattt atgacacatc | 540 |
| caacgtggct cctggagtcc cttttcgctt cagtggcagt gggtctggga cctcttattc | 600 |
| tctcacaatc aaccgaatgg aggctgagga tgctgccact tattactgcc aggagtggag | 660 |
| tggttatccg tacacgttcg gagggggac caagctggag ctgaaagcga agaaactgc | 720 |
| tgctgctaaa ttcgaacgcc agcacatgga cagctgactc gagcggccgc atcgtgactg | 780 |
| actgacgatc tgcctcgcgc gtttcggtga tgacggtgaa aacctctgac acatgcagct | 840 |
| cccggagacg gtcacagctt gtctgtaagc ggatgccggg agcagacaag cccgtcaggg | 900 |
| cgcgtcagcg ggtgttggcg ggtgtccggg ccccgccatg acccagtcac gtagcgatag | 960 |
| cggagtgtat aattcttgaa gacgaaaggg cctcgtgaat cgcctatttt tatagggtaa | 1020 |
| tgtcatgata ataatggttt cttaaacgtc aagggggcac ttttttcggga aatgtgcgcc | 1080 |
| gaaacccta atttgtttta tttttcaaaa tccatttcaa ttaagtttcc ccctcatgga | 1140 |
| aacaataacc cctggaaaaa aggctttcat taaatattga aaaaaggaa aaagttaaa | 1200 |
| aattatttca aaattttccc tgtgttcccc cctttatttt ccccttttt ttgcgggcca | 1260 |
| ttttttgccc ttttccctgg tttttttgc ccccccccc caaaaaaacc cccctggggt | 1320 |
| gaaaaaaaaa taaaaaaaaa aaatgtcttt aaaaaaaaat ttccaattt tgtggggggg | 1380 |
| gggccccccc aaaagagttg ggggggtttt ttaaaccact tctcccaaaa caacattggg | 1440 |
| tggagatatt tcttcttcac aaaa | 1464 |

<210> SEQ ID NO 25
<211> LENGTH: 1492
<212> TYPE: DNA
<213> ORGANISM: Homo sapiens

<400> SEQUENCE: 25

| ggtgggtaaa tttagcagca gcagtttctt tcgctttcag ctccagcttg gtcccccctc | 60 |
| cgaacgtgtc cggataacca ctccactcct ggcagtaata agtggcagca tcctcagcct | 120 |
| ccattcggtt gattgtgaga gaataagagg tcccagaccc actgccactg aagcgaaaag | 180 |
| ggactccagg agccacgttg gatgtgtcat aaatcaggag tctgggggag gatccaggct | 240 |

-continued

```
tctgttggta ccaatatatg taacgtatac ttgagctggc actgcaggtc atggtgaccc    300
tctcccctgg agatgcagac atgattgctg gagactgggt gagcacattt tcactgccac    360
cgccacacga tccaccgccg cagctaccac ccccgcctga ggagacggtg accgtggtcc    420
cttggcccca caagtcaaag tagcgcctgt agtagtcccc tctagcacag aaatagacag    480
cagagtcctc agatgtcagc ctagtgagct ccatataggc tgtgctggag gacttgtcta    540
cactcagtgt ggccctgccc ttgaacttct cattgtattc agtactcccc tctccaggaa    600
aaatccatcc aatccactca agtccctgtt caggcgtctg cctcacccag tctatatcat    660
aacttgtgaa gatgtagcca gaagccttgc aggacaactt cactgaagcc caggcttta    720
ccacttcagt tcctgactcc tgcagcttga cctcgggaat tccagaaagg gcctgcttga    780
acttctcctt tgcttcttcc atatctttct catgggcgga tccacgcgga accagatccg    840
attttggagg atggtcgcca ccaccaaacg tggcttgcca gccctggcaa ggccatgcta    900
tatacttgct ggatttcaag tacttatcaa tttgtgggaa tagcttcctt acgtttttt     960
aaaacaaact aattttggga acgcatccag gcccatttgg tccatgtatt aaaacaccat   1020
caaaaacctc ctacaacatg aaattccgga aggggtttac ataatccccc attttaaata   1080
ttgtttttat gacataaaac caatctttcc aaactttttt tcacattttc caggtaacct   1140
tggtaaaaaa aaaaccactt ttgaaaagtt tttcaaaatt cttttatta aaatgcaaat    1200
tttcccgaaa aaaccccctt atttctaaaa attcccaaaa acccgctccc ctttccaagc   1260
cctttgaaaa atttctttgc ccccccctc tttttgggg aacaaaaccc cccccacaa     1320
acttgggttg ggggtggttt ttgtgtccac gcccaaatat aaaaaaacag tataaattaa   1380
gatggggccc ccacatataa aaactgggg ggggttttt tatataattt tttaaaacac    1440
aacatccccc cccccccccc acatcccaca caaaataaaa tatataataa aa           1492
```

METHODS AND COMPOSITIONS FOR TARGETED TWO-DIMENSIONAL WESTERN BLOT ANALYSIS FOR EARLY CANCER DETECTION AND CANCER DIAGNOSIS UP TO TEN YEARS IN ADVANCE OF CLINICAL SYMPTOMS OF MALIGNANT DISEASE

CROSS-REFERENCE TO RELATED APPLICATIONS

None.

TECHNICAL FIELD OF THE INVENTION

The present invention relates in general to the field of cancer detection and diagnosis, and more particularly, to a functionalized single chain variable region recombinant ENOX2 antibody based on NADH-targeted detection.

STATEMENT OF FEDERALLY FUNDED RESEARCH

None.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on May 30, 2016, is named MNCE1002.txt and is 18 kilobytes in size.

BACKGROUND OF THE INVENTION

Without limiting the scope of the invention, its background is described in connection with cancer protein biochemistry.

There is a unique, growth-related family of cell surface hydroquinone or NADH oxidases with protein disulfide-thiol interchange activity referred to as ECTO-NOX proteins (for cell surface NADH oxidases) (Morre, 1998. Plasma Membrane Redox Systems and Their Role in Biological Stress and Disease (Asard, H., Berczi, A. and Caubergs, R. J., Eds) pp. 121-156, Kluwer Academic Publishers, Dordrecht, Netherlands; Morre and Morre, 2003. Free Radical Res. 37: 795-805). One member of the ECTO-NOX family, designated ENOX2 (for tumor associated) is specific to the surfaces of cancer cells and the sera of cancer patients (Morre et al., 1995. Proc. Natl. Acad. Sci. 92: 1831-1835; Bruno et al., 1992. Biochem. J. 284: 625-628). The presence of the ENOX2 protein has been demonstrated for several human tumor tissues (mammary carcinoma, prostate cancer, neuroblastoma, colon carcinoma and melanoma) (Cho et al., 2002. Cancer Immunol. Immunother. 51: 121-129); and serum analysis suggest a much broader association with human cancer (Morre, et al., 1997. Arch. Biochem. Biophys. 342: 224-230; Morre and Reust, 1997. J. Bioenerg. Biomemb. 29: 281-289).

ENOX proteins are ectoproteins anchored in the outer leaflet of the plasma membrane (Morre, 1965. Biochim. Biophys. Acta 1240: 201-208; FIG. 1). As is characteristic of other examples of ectoproteins (sialyl and galactosyl transferase, dipeptidylamino peptidase IV, etc.), the ENOX proteins are shed. They appear in soluble form in conditioned media of cultured cells (Cho et al., 2002. Cancer Immunol. Immunother. 51: 121-129) and in patient sera (Morre, et al., 1997. Arch. Biochem. Biophys. 342: 224-230; Morre and Reust, 1997. J. Bioenerg. Biomemb. 29: 281-289). The serum form of ENOX2 from cancer patients exhibits the same degree of drug responsiveness as does the membrane-associated form. Drug-responsive ENOX2 activities are seen in sera of a variety of human cancer patients, including patients with leukemia, lymphomas or solid tumors (prostate, breast, colon, lung, pancreas, ovarian, and liver) (Morre, et al., 1997. Arch. Biochem. Biophys. 342: 224-230; Morre and Reust, 1997. J. Bioenerg. Biomemb. 29: 281-289). The extreme stability and protease resistance of the ENOX2 protein (del Castillo-Olivares et al., 1998. Arch. Biochem. Biophys. 385: 125-140) may help explain its ability to accumulate in sera of cancer patients to readily detectable levels. In contrast, no drug-responsive NOX activities have been found in the sera of healthy volunteers or in the sera of patients with disorders other than neoplasia (Morre, et al., 1997. Arch. Biochem. Biophys. 342: 224-230; Morre and Reust, 1997. J. Bioenerg. Biomemb. 29: 281-289).

While the basis for the cancer specificity of cell surface ENOX2 was not previously determined, the concept was supported by several lines of evidence. Drug responsive ENOX2 activity has been rigorously determined to be absent from plasma membranes of non-transformed human and animal cells and tissues (Morre et al., 1995. Proc. Natl. Acad. Sci. 92: 1831-1835). ENOX2 proteins lack a transmembrane binding domain (Morre, et al., 2001. Arch. Biochem. Biophys. 392: 251-256) and are released from the cell surface by brief treatment at low pH (del Castillo-Olivares et al., 1998. Arch. Biochem. Biophys. 358: 125-140). A drug-responsive ENOX2 activity has not been detected in sera from healthy volunteers or patients with diseases other than cancer (Morre, et al., 1997. Arch. Biochem. Biophys. 342: 224-230; Morre and Reust, 1997. J. Bioenerg. Biomemb. 29: 281-289). Several ENOX2 antisera have identified the immunoreactive band at 34 kDa (the processed molecular weight of one of the cell surface forms of ENOX2) by Western blot analysis or immunoprecipitation when using transformed cells and tissues or sera of cancer patients as antigen source (Cho et al., 2002. Cancer Immunol. Immunother. 51: 121-129; Morre, et al., 2001. Arch. Biochem. Biophys. 392: 251-256; Chueh et al., 2002. Biochemistry 44: 3732-3741). The immunoreactive band at 34 kDa is absent with Western blot analysis or immunoprecipitation when using transformed cells and tissues or sera from healthy volunteers or patents with disorders other than cancer (Cho et al., 2002. Cancer Immunol. Immunother. 51: 121-129; Morre, et al., 2001. Arch. Biochem. Biophys. 392: 251-256; Chueh et al., 2002. Biochemistry 44: 3732-374). These antisera include a monoclonal antibody (Cho et al., 2002. Cancer Immunol. Immunother. 51: 121-129), single-chain variable region fragment (scFv) which reacts with the cell surface NADH oxidase from normal and neoplastic cells, polyclonal antisera made in response to expressed ENOX2 (Chueh et al., 2002. Biochemistry 44: 3732-374) and polyclonal peptide antisera to the conserved adenine nucleotide binding region of ENOX2 (Chueh et al., 2002. Biochemistry 44: 3732-374).

ENOX2 cDNA has been cloned (GenBank Accession No. AF207881; 11; U.S. Patent Publication 2003/0207340 A1). The derived molecular weight from the open reading frame is 70.1 kDa. Functional motifs include a quinone binding site, an adenine nucleotide binding site, and a CXXXXC cysteine pair as a potential protein disulfide-thiol interchange site based on site-directed mutagenesis (Chueh et al., 2002. Biochemistry 44: 3732-374). Based on available genomic information (Bird, 1999. Direct submission of human DNA sequence from clone 875H3 (part of APK1 antigen) to GenBank database at NCBI) the ENOX2 gene is located on chromosome X, and it is comprised of multiple exons (thirteen). It is known that there are a number of splice variant mRNAs and proteins expressed.

The hybridoma cell line that produces the tumor NADH oxidase-specific monoclonal antibody MAB 12.1 was deposited with the American Type Culture Collection, Manassas, Va., 20108 on Apr. 4, 2002, under the terms of the Budapest Treaty. This deposit is identified by Accession No. ATCC PTA-4206. The deposit will be maintained with restriction in the ATCC depository for a period of 30 years from the deposit date, or 5 years after the most recent request, or for the effective life of the patent, whichever is longer, and will be replaced if the deposit becomes non-viable during that period. This monoclonal antibody is described in U.S. Pat. No. 7,053,188, issued May 30, 2006, which is incorporated by reference herein.

Because cancer poses a significant threat to human health and because cancer results in significant economic costs, there is a long-felt need in the art for an effective, economical and technically simple system in which to assay for the presence and organ site of cancer.

SUMMARY OF THE INVENTION

The present invention includes methods for the analysis of a biological sample for the presence of particular transcript variants of the pan-cancer antigen known as ENOX2 (for tumor-specific NADH oxidase). The present method includes, e.g., a 2-dimensional gel electrophoresis and immunoblotting using an antibody specific for the pan-cancer ENOX2 antigen and the various isoforms, which characterize particular types of cancers. The methods of the present invention can also be applied to evaluate response to therapy, with decreasing amounts of ENOX2 isoform(s) reflecting successful treatment, as well as early detection of recurrent disease (reflected increased or reappearance of ENOX2-specific isoforms.

In one embodiment, the present invention includes a method for detecting benign to malignant transformation of a cancer in a subject, comprising the steps of: collecting sample from the subject prior to electrophoretic protein separation; activating electrophoretically separated ENOX2 transcript variants with an ENOX2 electron donor; and detecting the presence of the one or more activated ENOX2 transcript variants using a pan-ENOX2 detectable binding reagent, wherein the presence of one or more activated ENOX2 transcript variants in the sample is indicative of the malignant transformation of the cancer, whereby a 10 to 100 fold increase in detection sensitivity is obtained for the one or more activated ENOX2 transcript variants when compared to equivalent non-activated ENOX2 transcript variants. In one aspect, the ENOX2 electron donor required to activate the ENOX2 transcript variants is selected from at least one of a reduced pyridine nucleotide, NADH, NAD (P)H, or a synthetic substrate that is an ENOX2 electron donor, and detecting the one or more activated ENOX2 transcript variants on the 2D blot, wherein the final concentration of NADH or NAD(P)H is in the range 10 µM to 50 µM. In another aspect, the method further comprises performing two dimensional (2D) electrophoretic protein separation and blotting onto a film or paper. In another aspect, the pan-ENOX2 detectable binding reagent comprises SEQ ID NO:1. In another aspect, the sample is a blood, serum, plasma, urine, cerebrospinal fluid or other body fluid. In another aspect, the pan-ENOX2 detectable binding reagent comprises an anti-ENOX2 scFv fusion protein that is: non-aggregating at between 4° C. and 40° C.; comprises a functional linker between heavy and light chain portions of the ScFv fusion protein comprised primarily of amino acids with small side chains (Gly/Ser) containing, in addition, two cysteine residues (C) spaced as either CXXXXC or CXXXXXC; and is capable of forming an interchain disulfide bond with the protein disulfide-thiol interchange functional motif of ENOX2. In another aspect, the pan-ENOX2 detectable binding reagent comprises an scFv of SEQ ID NO:11, wherein the stability, binding efficiency, and shelf life of the scFv of SEQ ID NO:1 is improved by storing in 50% at −70° C. glycerol to prevent aggregation. In another aspect, the step of concentrating the blood, serum, or plasma sample is defined further as concentrating the one or more ENOX2 transcript variants using a nickel-agarose substrate to bind and concentrate the one or more ENOX2 transcript variants. In another aspect, the method further comprises detecting the cancer and/or determining a tissue of origin of a human cancer at least one year in advance of clinical symptoms. In another aspect, the method further comprises detecting the cancer and/or determining a tissue of origin of a human cancer at least one year (e.g., 2, 3, 4, 5, 6, 7, 8, 9, 10 or 20 years) in advance of clinical symptoms. In another aspect, the method further comprises determining a tissue of origin of one or more cancers of unknown primary (CUP). In another aspect, the method further comprises screening for at least one of: early cancer in populations with family cancer histories, environmental exposures, or in a general population. In another aspect, the method further comprises determining a tissue of origin of the one or more activated ENOX2 transcript variants based on the presence of ENOX2 transcript variants as set forth in the following Table 1:

TABLE 1

Ranges for Molecular Weight (MW) and Isoelectric Point (Pi) Determined for Sera of Patients Diagnosed with 24 Different Cancers Representing 20 Different Tissues of Origin

| | | RANGES | | | | | |
|---|---|---|---|---|---|---|---|
| | | Protein 1 | | Protein 2 | | Protein 3 | |
| Cancers | N | MW (kDa) | Pi (PH) | MW (kDa) | Pi (PH) | MW (kDa) | Pi (pH) |
| Bladder | 37 | 63-66 | 4.2-5.6[1] | 42-48 | 4.1-4.8[1] | | |
| *Blood Cell (Total) | (117) | 34-47 | 3.5-4.6 | | | | |
| Breast | 682 | 64-69 | 4.2-4.9 | | | | |
| Cervical | 47 | 90-100 | 4.2-5.4 | | | | |

TABLE 1-continued

Ranges for Molecular Weight (MW) and Isoelectric Point (Pi) Determined
for Sera of Patients Diagnosed with 24 Different Cancers Representing 20 Different Tissues
of Origin

| | | RANGES | | | | | |
|---|---|---|---|---|---|---|---|
| | | Protein 1 | | Protein 2 | | Protein 3 | |
| Cancers | N | MW (kDa) | Pi (PH) | MW (kDa) | Pi (PH) | MW (kDa) | Pi (pH) |
| Colorectal | 125 | 80-96 | 4.4-5.4 | 50-65 | 4.2-5.3 | 33-46 | 3.8-5.2 |
| Esophageal | 26 | 42-47 | 4.6-5.2 | | | | |
| Gastric | 26 | 120-188 | 4.7-5.5 | 50-62 | 4.5-5.6 | 45-53 | 2.4-3.6 |
| Hepatocellular | 31 | 58-70 | 4.5-5.0 | 34-40 | 4.1-5.2 | | |
| Leukemias | 36 | 34-45 | 3.5-4.5 | | | | |
| **Lung, Non-Small Cell | 55 | 53 | 4.7-5.3 | | | | |
| **Lung, Non-Small Cell | 270 | 54-56 | 4.6-5.3 | | | | |
| Lung, Small Cell | 27 | 52-53 | 4.1-4.6 | | | | |
| Lymphomas | 56 | 43-45 | 3.5-4.5 | | | | |
| Melanoma | 51 | 37-41 | 4.6-5.3 | | | | |
| Mesothelioma | 27 | 60-68 | 3.8-4.1 | 38-44 | 3.8-4.6 | | |
| Myelomas | 25 | 40-45 | 3.9-4.6 | | | | |
| Ovarian | 115 | 72-90 | 3.7-5.0 | 37-47 | 3.7-5.0 | | |
| Pancreatic | 75 | 48-51 | 3.9-5.4 | | | | |
| Prostate | 361 | 71-88 | 5.1-6.5 | | | | |
| Renal Cell (Kidney) | 31 | 69-73 | 4.7-5.4 | 54-61 | 4.1-5.2 | 38-43 | 3.7-4.3 |
| Sarcoma | 29 | 50-55 | 5.2-5.6 | 37-45 | 4.3-4.9 | | |
| Squamous Cell | 51 | 57-68 | 5.0-5.4 | | | | |
| Testicular Germ Cell | 25 | 61-62 | 5.0-5.4 | 40-45 | 4.4-4.7 | | |
| Thyroid Follicular | 25 | 48-56 | 4.7-5.1 | 37-42 | 4.5-5.2 | | |
| Thyroid Papillary | 27 | 56-67 | 4.5-5.0 | 37-44 | 3.2-3.6 | | |
| ***Uterine (Endometrial) | 26 | 63-66 | 4.2-4.9[2] | 41-48 | 4.4-5.6[2] | | |
| ***Uterine (Endometrial) | 57 | 67-71 | 4.2-5.1 | 41-48 | 3.7-5.4 | | |
| Total | 2460 | | | | | | |

*Blood cell cancers include lymphomas, leukemias and myelomas already represented in the totals.
**Non-Small Cell Lung cancers are in two subsets to avoid molecular weight overlap with small cell lung cancer.
***Uterine cancers are in two subsets based on molecular weight to avoid overlap with bladder cancer (see footnotes 1 and 2).
1. Isoelectric point pH of Protein 1 ≥ Protein 2.
2. Isoelectric point pH of Protein 1 < Protein 2.

In another aspect, the method further comprises resolving proteins at 53 and/or 79 to 85 kDa as total protein loading controls. In another aspect, the method further comprises distinguishing between distant metastases and multiple primary cancers based on the presence of the one or more activated ENOX2 transcript variants. In another aspect, the method further comprises detecting stage 0 and stage 1 cancers and determining the tissue of origin of the cancer. In another aspect, an incidence of false positives and confirmed false negatives of the predicted cancer is less than 1%. In another aspect, the sensitivity of the method for detecting the cancer is greater than 95%. In another aspect, the sensitivity of the method detects the presence of 2 million cancer cells or less. In another aspect, the method further comprises monitoring the reemergence of the cancer, therein the presence of 2 million or less cancer cells is detectable based on the reemergence of the one or more activated ENOX2 transcript variants. In another aspect, the method further comprises determining between malignant and benign early neoplastic lesions, wherein if a benign legion is detected a step of performing surgery, chemotherapy, or radiation therapy may be avoided. In another aspect, the method further comprises determining an early indication of prostate cancer. In another aspect, the method further comprises determining a ductile mammary carcinoma in situ and in need of curative early intervention to potentially avoid surgery, the need for radiation or chemotherapy, prior to the development of ductal mammary carcinoma. In another aspect, the benign to malignant transformation is detected at least one year before development of clinical symptoms. In another aspect, the tissue of origin of the cancer detected is selected from at least one of bladder, blood cell, lymphomas, leukemias, multiple myelomas and myelomas breast, cervical, colorectal, esophageal, gastric, hepatocellular, lung, non-small cell, melanoma, mesothelioma, ovarian, pancreatic, prostate, renal cell (kidney), sarcoma, squamous cell, testicular germ cell, thyroid follicular, thyroid papillary, or uterine (endometrial).

Yet another embodiment of the present invention includes a calibrated method of quantitation of ENOX2 transcript variants on a western blot comprising: subjecting a sample from the subject concentrated sample to electrophoretic protein separation; western blotting the electrophoretically separated proteins onto a protein capture film or paper; activating one or more ENOX2 transcript variants on the protein capture film or paper with a reduced ENOX2 substrate; and detecting the presence of the one or more activated ENOX2 transcript variants using a pan-ENOX2 detectable binding reagent, wherein a presence of one or more activated ENOX2 transcript variants in the blood, serum, or plasma sample is indicative of the malignant transformation of the cancer, wherein a 10 to 100 fold increase in detection sensitivity for ENOX2 is obtained when compared to the non-activated ENOX2, wherein the amount of the amount of one or more activated ENOX2 transcript variants is calibrated based on a spot diameter and an intensity of the ENOX2 transcript variant on the protein capture film or paper when compared to a known amount of the one or more ENOX2 transcript variants. In one aspect, the spot diameter is compared to a standard curve of recombinant ENOX2. In another aspect, the spot diameter and the log of the mass of ENOX2 are linearly correlated.

Yet another embodiment of the present invention includes a method for determining the tissue of origin of a cancer in a subject comprising: subjecting proteins in a sample from the subject to a two-dimensional (2D) molecular weight and isoelectric point electrophoretic protein separation; transferring the proteins to a protein capture film or paper; activating the electrophoretically separated ENOX2 transcript variants by incubation with an ENOX2 electron donor on the protein capture film or paper; detecting the activated ENOX2 transcript variants; and determining the tissue of origin of the cancer based on the presence of one or more activated ENOX2 transcript variants in the sample from the Table 1, wherein activation of the one or more ENOX2 transcript variants in situ increases the detection sensitivity by 10 to 100 fold when compared to non-activated ENOX2 transcript variants. In another aspect, the ENOX2 electron donor required to activate the ENOX2 transcript variants is selected from at least one of a reduced pyridine nucleotide, NADH, NAD(P)H, or a synthetic substrate that is an ENOX2 electron donor, and detecting the one or more activated ENOX2 transcript variants on the 2D blot, wherein the final concentration of NADH or NAD(P)H is in the range 10 µM to 50 µM. In another aspect, the method further comprises performing two dimensional (2D) electrophoretic protein separation and blotting onto a film or paper, wherein the ENOX2 electron donor is selected from at least one of a reduced pyridine nucleotide, NADH, NAD(P)H, or a synthetic substrate that is an ENOX2 electron donor, and detecting the one or more activated ENOX2 transcript variants on the 2D blot, wherein the final concentration of NADH or NAD(P)H is in the range 10 µM to 50 µM. In another aspect, the pan-ENOX2 detectable binding reagent comprises SEQ ID NO:11. In another aspect, the pan-ENOX2 detectable binding reagent comprises an anti-ENOX2 scFv fusion protein is: non-aggregating at between 4° C. and 40° C.: comprises a small side chain (Gly/Ser) amino acid residues containing two cysteines (C) spaced as either CXXXXC or CXXXXXC; and is capable of forming interchain disulfide bonds with the protein disulfide-thiol interchange functional motif of ENOX2. In another aspect, the pan-ENOX2 detectable binding reagent comprises an scFv of SEQ ID NO:11, wherein the stability, binding efficiency, and shelf life of the scFv of SEQ ID NO:11 is improved by storing in 50% glycerol at −70° C. to prevent aggregation. In another aspect, the step of concentrating the sample is defined further as concentrating the one or more ENOX2 transcript variants using a nickel-agarose substrate to bind and concentrate the one or more ENOX2 transcript variants. In another aspect, the method further comprises detecting the cancer and/or determining a tissue of origin of a human cancer at least one year in advance of clinical symptoms. In another aspect, the sample is a blood, serum, plasma, urine, cerebrospinal fluid or a body fluid.

Yet another embodiment of the present invention includes a blot comprising one or more electrophoretically separated proteins from a concentrated sample from a subject, wherein the blot is exposed to a pan-ENOX2 detecting reagent and to a reducing substrate for ENOX2 that activates the ENOX2 transcript variants on the blot, wherein the blot is analyzed for the present of one or more activated ENOX2 transcript variants from Table 1, wherein the presence of the one or more activated ENOX2 transcript variants is used to detect and determine a tissue of origin of a human cancer at least one year in advance of clinical symptoms, and the activation of the one or more ENOX2 transcript variants in situ increases the detection sensitivity by 10 to 100 fold when compared to non-activated ENOX2 transcript variants.

BRIEF DESCRIPTION OF THE DRAWINGS

For a more complete understanding of the features and advantages of the present invention, reference is now made to the detailed description of the invention along with the accompanying figures and in which:

FIGS. 8A to 8J show western blots of 2-D gel electrophoresis/western blots of sera from cancer patients analyzed individually. Cancer sites are presented in the order of decreasing molecular weight of the major transcript variant present. FIG. 8A. Cervical cancer. FIG. 8B. Ovarian cancer. FIG. 8C. Prostate cancer. FIG. 8D. Breast cancer. FIG. 8E. Non-small cell lung cancer. FIG. 8F. Small cell lung cancer. FIG. 8G. Pancreatic cancer. FIG. 8H. Colon cancer. FIG. 8I. Non-Hodgkin lymphoma. FIG. 8J. Melanoma. The approximate location of unreactive (at background) albumin (Ab) is labeled for comparison. Approximately 180 non-cancer patient sera were analyzed in parallel without evidence of proteins indicative of specific transcript variants for comparison as positive controls.

FIGS. 9A and 9B show analytical gel electrophoresis and immunoblots of patient sera. FIG. 9A. Sera from a patient with non-small cell lung cancer contains a 54 kDa, isoelectric point pH 5.1 transcript variant (arrow). FIG. 9B. Sera from a patient with small cell lung cancer contains a 52 kDa, isoelectric point 4.3 transcript variant (arrow). The reference spots to the right, MW 52 kDa and isoelectric point pH 4.1 are $\alpha$1-antitrypsin inhibitor. Albumin and other serum proteins are unreactive.

In FIG. 12B, with the conventional linker lacking cysteines, no evidence of cross-linking under identical reaction conditions was observed.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The field of this invention is a serum-based assay for early pan-cancer diagnosis of cancer that permits detection of cancer up to ten years in advance of clinical symptoms of malignant disease based on a specific functionalized single chain variable region recombinant antibody targeted to a cancer-specific family of cell surface ENOX2 proteins whereby molecular weights and isoelectric points of tissue of origin-specific transcript variants determined by using two-dimensional gel electrophoresis with an ENOX2-specific recombinant scFv antibody combined with NADH-targeted technology providing ten- to 100-fold enhanced sensitivity over the previously developed protocols.

Figure 6:
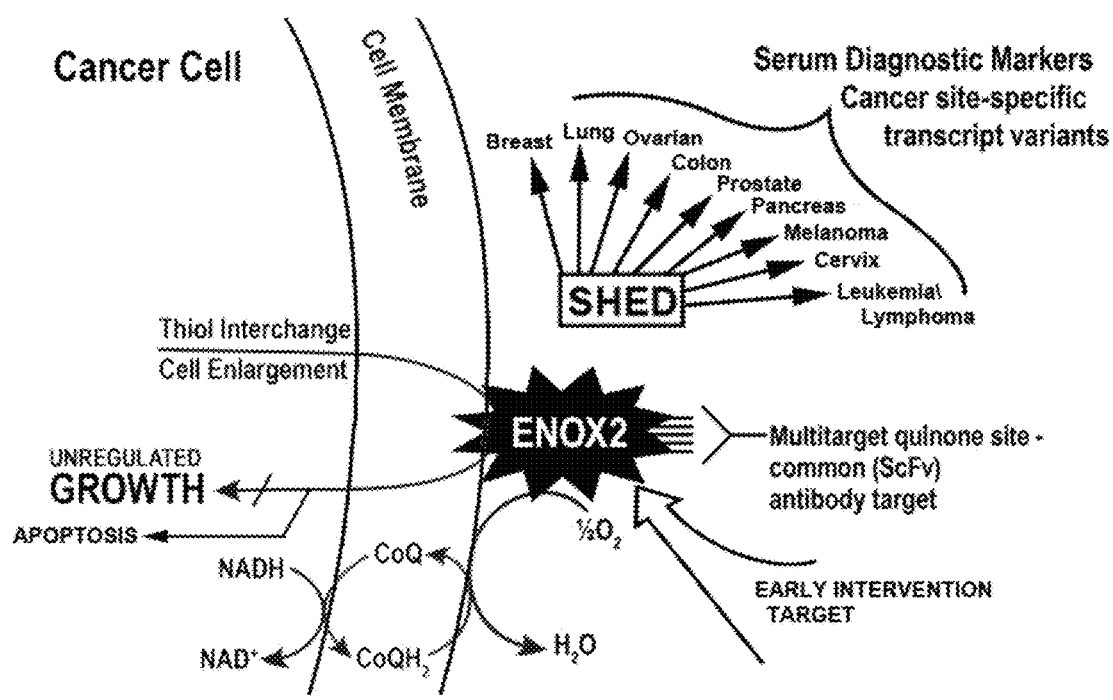
FIG. 6 is a schematic representation of the utility of the ENOX2 family of cancer-specific, cell surface proteins for early diagnosis and early intervention of cancer. Cancer site-specific transcript variants of ENOX2 are shed into the serum to permit early detection and diagnosis. The ENOX2 proteins of origin at the cell surface act as terminal oxidases of plasma membrane electron transport functions essential to the unregulated growth of cancer. When the ENOX2 proteins are inhibited, as for example through EGCg/Capsicum synergies, the unregulated growth ceases and the cancer cells undergo programmed cell death (apoptosis).

Ecto-Nicotinamide Adenine Dinucleotide Oxidase Disulfide Thiol Exchanger 2 (ENOX2) (GenBank accession no. AF207881; Chueh et al., 2002) also known as Tumor Associated Nicotinamide Adenine Dinucleotide Oxidase (ENOX2) is ideally suited as a target for early diagnosis as well as for early preventive intervention (FIG. 6). The proteins are expressed on the cell surface of malignancies and detectable in the serum of patients with cancer (Cho et al., 2002). ENOX2 proteins are terminal hydroquinone oxidases of plasma membrane electron transport. From the standpoint of early intervention, they are important in the growth and enlargement of tumor cells (Morre and Morre, 2003; Tang et al., 2007. *Biochemistry* 46:12337-12346; 2008. *Oncol. Res.* 16:557-567). Our approach using ENOX2, as a target for both early detection and for early interventions, is based on these properties (Cho et al., 2002; Morre and Morre, 2003; reviewed by Davies and Bozzo, 2005. *Drug News Perspect* 19: 223-225). While ENXO2 presence provides a non-invasive approach to cancer detection, without methodology to identify cancer site-specific ENOX2 forms, it did not offer an indication as to cancer type or location.

The present invention provides a method for the analysis of a biological sample for the presence of particular isoforms of the pan-cancer antigen known as ENOX2 (for tumor-specific NADH oxidase). The present method entails 2-dimensional gel electrophoresis and immunoblotting using an antibody specific for the pan-cancer ENOX2 antigen and the various isoforms which characterize particular types of cancers. As specifically exemplified, about 30 μL of sera are loaded for analysis.

ENOX2 transcript variants are identified on the basis of their molecular weights and isoelectric point with detection using a ENOX2-specific monoclonal antibody (MAb) (U.S.

Pat. No. 7,053,188), using single chain variable region (scFv) fragment which recognizes all cell surface NOX proteins (both age-related, normal cell and neoplasia specific NADH oxidase) or using polyclonal sera raised against ENOX2. The ECTO-NOX proteins are first enriched and concentrated from a biological sample, desirably a serum sample, by binding to nickel-agarose and then eluting. After release of the proteins from the nickel agarose by vortexing, the proteins are separated in the first dimension by isoelectric focusing and in the second dimension by polyacrylamide gel electrophoresis. As specifically exemplified herein, the isoelectric focusing step is over a pH range from 3 to 10, and size separation is over a 10% polyacrylamide gel. Most of the cancer-specific ENOX2 isoforms exhibit isoelectric points in a very narrow range between pH 3.9 and 6.3 but differ in molecular weight from 34 to 136 kDa. In the 2D gel system specifically exemplified, the cancer-specific isoforms are located in Quadrants I (relatively high molecular weight material) and IV (lower molecular weight material, notably the range of 30 to 50 kDa. IgG heavy chains (Quadrant II and IgG light chains (Quadrant III) cross react with the scFv antibody and along with reference proteins at 53 and 79 to 85 kDa serve as loading controls. The absence of all ENOX2 isoforms indicates the absence of cancer or a cumulative cancer size below the limit of detection in the assay. The presence of an ENOX2 isoform indicates the presence of cancer. The particular molecular weight present in a serum sample or a particular combination of isoforms provides an indication of the cell type or tissue of origin of the cancer. The method not only determines cancer presence, but also the method of the present invention provides diagnostic information concerning the tissue of origin. At present there are no other pan cancer (all forms of human cancer) tests with these particular capabilities. ENOX2 transcript variants with apparent molecular weights in the range of 64-69 kDa. pH in the range of 4.2-4.9 are associated with breast cancer. ENOX2 transcript variants of 52-53 kDa, pH 4.1-4.6 is associated with small cell lung cancer. An ENOX2 transcript variant of 54-56 kDa, pH 4.6-5.3 is associated with non-small cell lung cancer. Two ENOX2 transcript variants of about 72-90 kDa and 37-47 kDa, isoelectric point pH 3.7-5.0 for both, characterize ovarian cancer. ENOX2 transcript variants of 71-88 kDa, pH 5.1-6.5 are associated with prostate cancer. An ENOX2 transcript variant of about 90-100 kDa, pH 4.2-5.4 signals cervical cancer. Three ENOX2 transcript variants of about 80-96 kDa, pH 4.4-5.4; 50-65 kDa, pH 4.2-5.3; and 33-46 kDa, pH 3.8-5.2 are characteristic of colon cancer. Where a patient is suspected of having cancer, the 2D gel electrophoresis/immunological analysis of a biological sample, advantageously a serum sample will reveal both cancer presence and organ site with the present invention.

Method 1—Ten- to 100-Fold Increase in Sensitivity and Specificity of the Western Blot Detection Protocol.

Using the present invention a ten- to 100-fold increase in sensitivity and specificity of the western blot detection protocol was derived from an observation that there was a delay time of the inhibition of NADH oxidation following exposure of serum ENOX2 to an antibody combining site inhibitory ligand. The inhibition was observed to occur at various time between 0 and 22 minutes (22 minutes is the length of the ENOX 2 activity cycle; (Wang et al., 2001. Biochim. Biophys. Acta 1539:i92-204) during a 30 minute incubation. Thus, the time during each 22 min activity cycle where the EEMTE antibody combining site is available for combination with antibody is relatively brief, and in the order of less than 5 minutes. Also, the ENOX2 protein must be active in order for the antibody to gain access to the binding site during this relatively short window of opportunity.

Table 2 shows the activity of ENOX2 at the five activity maxima during 5 successive 22 minutes activity cycles following antibody addition.

|  | nanomoles/min/mg protein | | | | |
| --- | --- | --- | --- | --- | --- |
|  | Maximum 1 | Maximum 2 | Maximum 3 | Maximum 4 | Maximum 5 |
| Cycle 1 |  |  |  |  | 1.00 |
| Cycle 2 | 1.00 | 1.25 | 0.75 | 0.90 | 0.40 |
| Cycle 3 | 0.50 | 0.25 | 0.30 | 0.25 | 0.25 |
| Cycle 4 | 0.10 | 0.50 | 0.25 | 0.25 | 0.05 |
| Cycle 5 | 0.10 | 0.05 | 0.30 | 0.00 | 0.30 |

Inhibition occurs at maximum 4 within the 22 min activity cycle. Thus, antibody binding must occur exclusively during maximum 4 since maximum 5 is the first maximum to be inhibited. Antibody addition at maximum 5 had no effect nor did antibody addition before maximum 4. A corollary of the above result is that antibody will not bind or will bind only poorly to inactive ENOX2 transcript variants. Therefore, steps were initiated to render ENOX2 on western blots active during incubation with antibody.

In order to maintain an active ENOX2 during western blotting with antibody, following blocking for 10 minutes with 1% milk and two rinses with TBST to remove excess milk, reduced pyridine nucleotides [NAD(P)H] were added at a concentration of 15 μM during incubation with the primary scFv antibody. NADH is preferred at a final concentration in the range of 10 μM. Incubation of the blot with antibody with or without shaking at any temperature between 4° C. and 40° C. for times of 1 to 16 hours depending on the concentration of NADH, the temperature and the antibody titer, preferably with incubation at 4° C. overnight (approximately 16 hours) with shaking.

The cancer diagnostic system of the present invention utilizes two-dimensional polyacrylamide gel electrophoretic techniques for the separation of proteins in human sera to generate cancer-specific isoform patterns and compositions indicative of cancer presence, tumor type, disease severity and therapeutic response. The protocol is designed for the detection of at least 26 cancer-specific patterns of ENOX2 transcript variants each denoting a different tumor type representing 20 different tissue of cancer origin, which are resolved to indicate cancer presence and origin of the primary cancer. This specification illustrates the process of the transcript-resolving two-dimensional gel electrophoresis protocol and subsequent immunoanalysis to detect ENOX2 transcript variants that reflect particular cancers.

Two-dimensional gel electrophoresis separates by displacement in two dimensions oriented at right angles to one another and immunoblotting identifies the ENOX2 isoforms. In the first dimension variants are separated by isoelectric point (pI) according to charge by isoelectric focusing (IEF). The variants are then separated according to molecular weight in kilodaltons (kDa) by SDS-PAGE in a second dimension. The isoforms are then blotted onto a nitrocellulose membrane for further analysis using the pan-cancer specific antibody preparation containing a functional linker that stabilizes antibody binding to the transcript variants.

The opportunity to simultaneously determine both cancer presence and cancer tissue of origin emerged as a result of 2-dimensional gel electrophoretic separations where western blots with a pan ENOX2 recombinant single chain variable region (scFv) antibody carrying an S tag (FIG. 7) was employed for detection (Hostetler et al., 2009. *Clin. Proteomics* 5: 46-51). The antibody cross reacted with all known ENOX2 transcript variants from hematological and solid tumors of human origin but, of itself, did not differentiate among different kinds of cancers. Analyses using this antibody, when combined with two-dimensional gel electrophoretic separation, revealed specific species of ENOX2 proteins subsequently identified as transcript variants, each with a characteristic molecular weight and isoelectric point indicative of a particular form of cancer (Table 1).

Method 2—ENOX Transcript Variants of Specific Molecular Weights and Isoelectric Points are Produced Uniquely by Patients with Cancer.

The transcript variants are shed into the circulation and have the potential to serve as definitive, non-invasive and sensitive serum markers for early detection of both primary and recurrent cancer in at risk populations with a low incidence of both false positives, and false negatives as they are molecular signature molecules produced specifically by cancer cells and absent from non-cancer cells.

As the 2-D-western blot protocol detects cancer early, well in advance of clinical symptoms, the opportunity to combine early detection with early intervention as a potentially curative prevention strategy for cancer is provided whereby elimination of the disease in its very earliest stages is uniquely possible.

Figure 2:
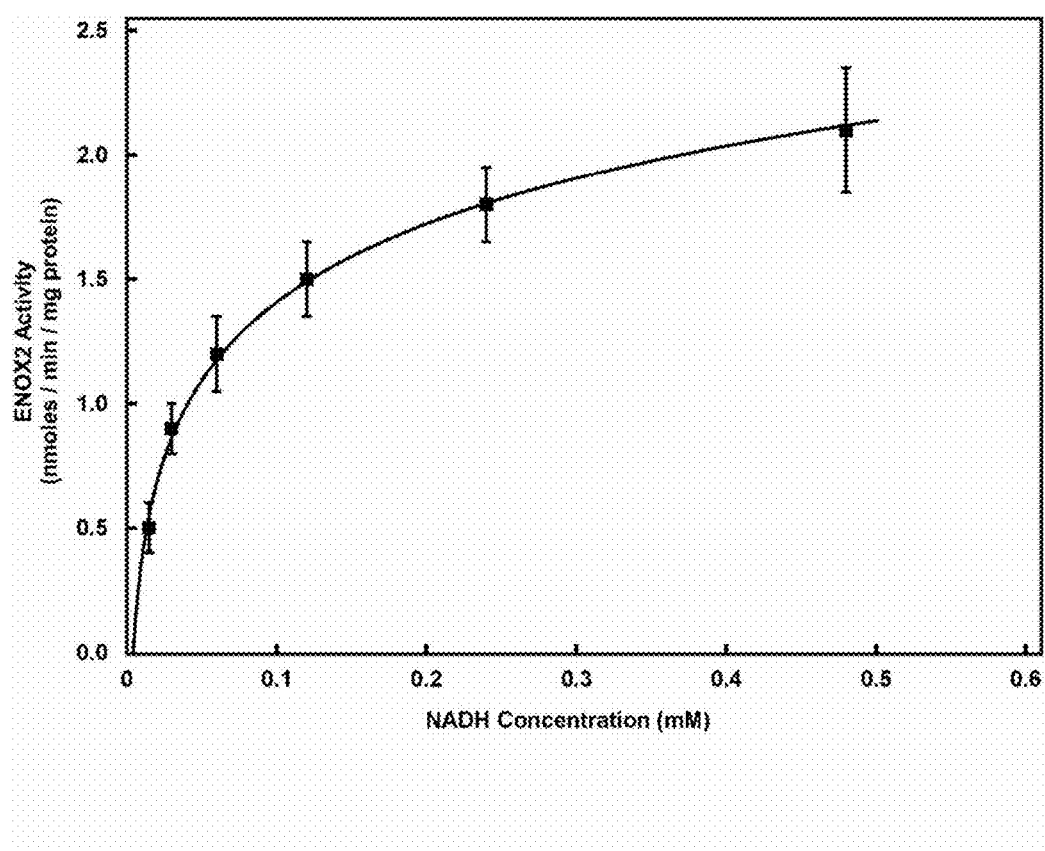
FIG. 2 is a graph that depicts the relationship of ENOX2 activity and concentration of NADH. Maximum activity was achieved at about 500 µM NADH with a kM of approximately 0.8 µM (see FIG. 3 for determination of kM).

FIG. 2 is a graph that depicts the relationship of ENOX2 activity and concentration of NADH. Maximum activity was achieved at about 500 μM NADH with a kM of approximately 0.8 μM (see FIG. 3 for determination of kM).

Figure 3:
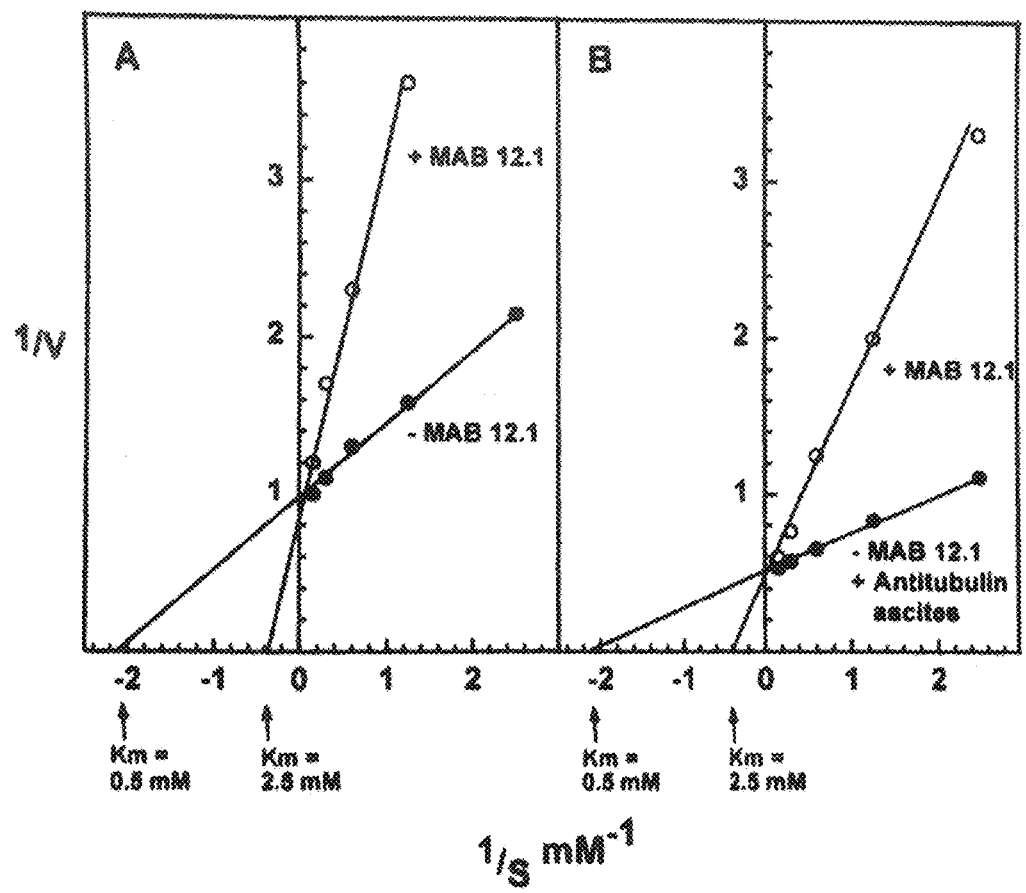
FIG. 3 is graph that shows a double reciprocal Lineweaver-Burke plot of ENOX2 activity (nanomoles/min/mg protein) V versus mM substrate concentration S yielding a kM of approximately 0.8 mM. The ordinate intercept being the same or similar for with and without antibody demonstrate that the antibody competes with the NADH substrate for the active site providing evidence for the substrate and antibody combining site being in the same region of the ENOX2 sequence.

FIG. 3 is graph that shows a double reciprocal Lineweaver-Burke plot of ENOX2 activity (nanomoles/min/mg protein) V versus mM substrate concentration S yielding a kM of approximately 0.8 mM. The ordinate intercept being the same or similar for with and without antibody demonstrate that the antibody competes with the NADH substrate for the active site providing evidence for the substrate and antibody combining site being in the same region of the ENOX2 sequence.

Figure 4:
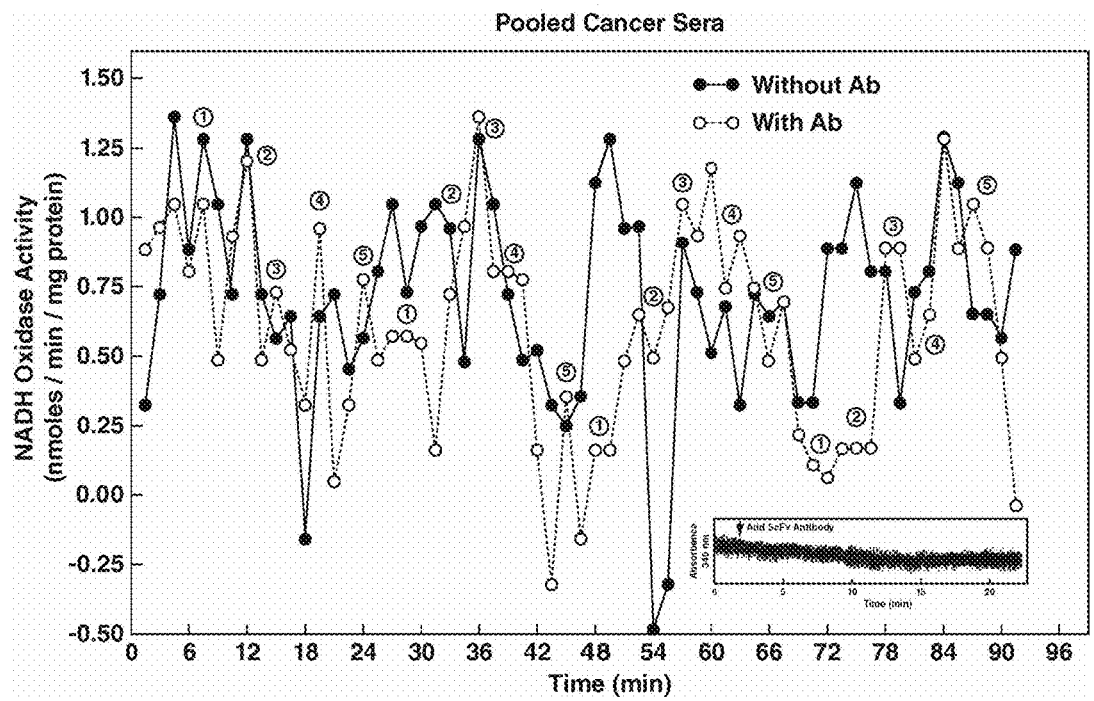
FIG. 4 is graph that shows a representation of ENOX2 activity as a function of time to illustrate five maxima of the ENOX2 activity cycle of pooled cancer sera. As quantitated in Table 1, inhibition occurs at maximum 4 within the 22 min activity cycle. Thus, antibody binding must occur exclusively during maximum 4 since maximum 5 is the first maximum to be inhibited. Antibody addition at maximum 5 had no effect nor did antibody addition before maximum 4.

FIG. 4 is graph that shows a representation of ENOX2 activity as a function of time to illustrate five maxima of the ENOX2 activity cycle of pooled cancer sera. As quantitated in Table 1, inhibition occurs at maximum 4 within the 22 minutes activity cycle. Thus, antibody binding must occur exclusively during maximum 4 since maximum 5 is the first maximum to be inhibited. Antibody addition at maximum 5 had no effect nor did antibody addition before maximum 4.

Figure 5:
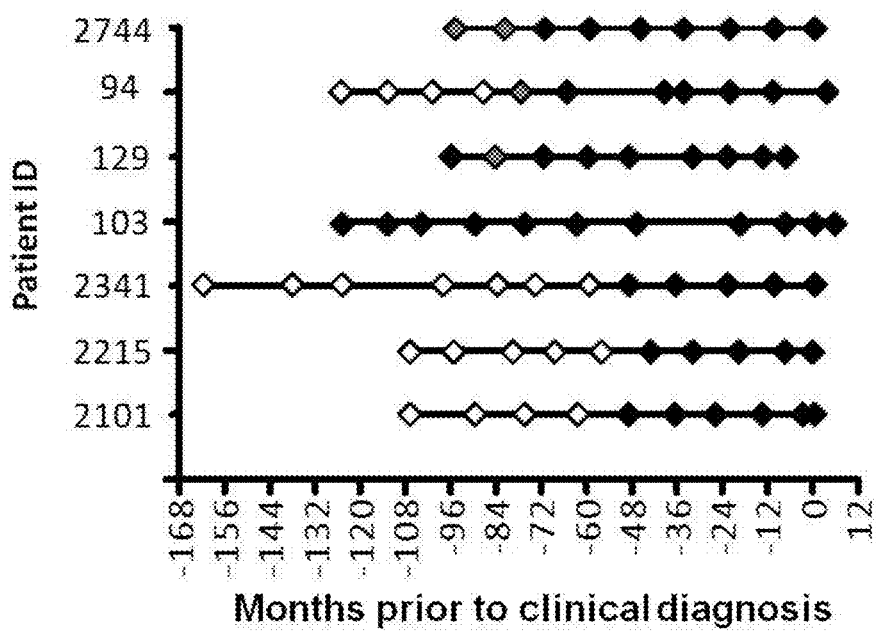
FIG. 5 is graph that depicts early detection of malignant mesothelioma in asbestos workers up to 10 years in advance of clinical symptoms. Serial assays of seven male subjects, median age of diagnosis 67 years, beginning 168 to 96 months before diagnosis of asbestos-induced malignant mesothelioma are represented. Solid symbols—both protein 1 and protein 2 characteristic of malignant mesothelioma, evident. Open symbols—neither protein 1 nor protein 2 evident. Shaded symbols—only protein 1 evident.

FIG. 5 is graph that depicts early detection of malignant mesothelioma in asbestos workers up to 10 years in advance of clinical symptoms. Serial assays of seven male subjects, median age of diagnosis 67 years, beginning 168 to 96 months before diagnosis of asbestos-induced malignant mesothelioma are represented. Solid symbols—both protein 1 and protein 2 characteristic of malignant mesothelioma, evident. Open symbols—neither protein 1 nor protein 2 evident. Shaded symbols—only protein 1 evident.

Figure 7:
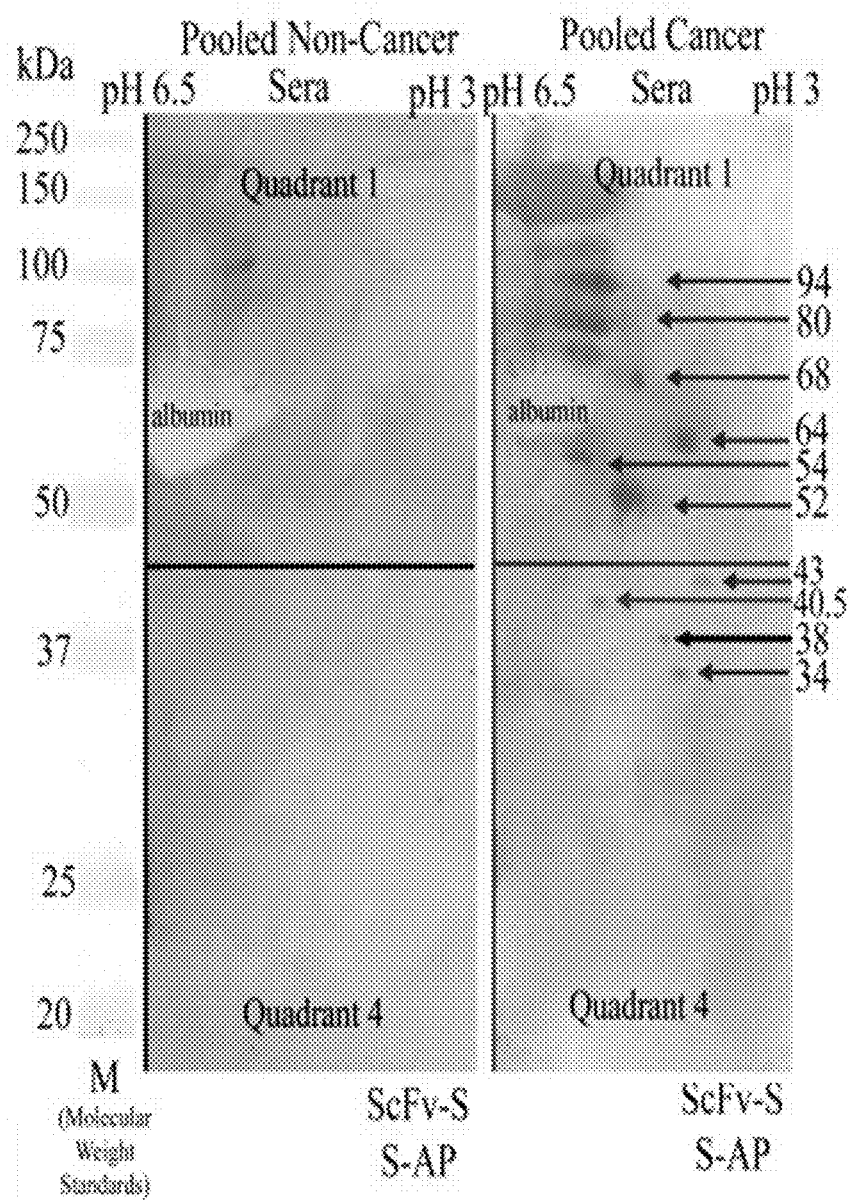
FIG. 7 provides a 2-Dimensional gel/western blot of ENOX2 transcript variants comparing pooled non-cancer (left panels) and pooled cancer representing major carcinomas plus leukemias and lymphomas (right panels) patient sera. The approximate location of unreactive (at background) albumin is labeled for comparison. ENOX2 reactive proteins are restricted to quadrants I and IV. Detection use recombinant scFv-S(S-tag peptide: His-Glu-Ala-Ala-Lys- Phe-Gln-Arg-Glu-His) antibody linked with alkaline phosphatase. The approximately 10 ENOX2 transcript variants of the pooled cancer sera are absent from non-cancer (A) and are cancer site-specific.

Analytical 2-D gel electrophoresis and immunoblotting of ENOX proteins from a mixed population of cancer patients (bladder, blood cell (leukemias, lymphomas, and myelomas), breast, cervical, colorectal, esophageal, gastric, hepatocellular, lung, melanoma, ovarian, pancreatic, prostate, renal cell (kidney), sarcoma, squamous cell, testicular germ cell, thyroid, and uterine (endometrial) revealed multiple species of acidic proteins of molecular weight between 34 and 100 kDa in quadrants I and IV (FIG. 7, right panels), none of which were present in sera of non-cancer patients (FIG. 7, left panels). Separation in the first dimension was by isoelectric focusing over the pH range of 3 to 10 and separation in the second dimension was by 10 percent SDS-PAGE. Isoelectric points of the ENOX2 transcript variants were in the range of 3.2 to 6.3. The principal reactive proteins other than the ENOX2 forms were a 53 kDa isoelectric point pH 4.1, mostly phosphorylated alpha-fetuin (Labeled "R" in FIG. 8) which served as a convenient loading control and isoelectric point reference and a 79-85 kDa, isoelectric point pH 6.8 serotransferrin which served as a second point of reference for loading and as an isoelectric point reference. The two cross reactive reference proteins are present in a majority of sera and plasma of both cancer and non-cancer subjects. Albumin and other serum proteins normally do not react when present in low amounts. On some blots, the recombinant scFv was weakly cross-reactive with heavy (ca. 52 kDa) and light (ca. 25 kDa) immunoglobulin chain proteins.

FIGS. 8A to 8J show western blots of 2-D gel electrophoresis/western blots of sera from cancer patients analyzed individually. Cancer sites are presented in the order of decreasing molecular weight of the major transcript variant present. FIG. 8A. Cervical cancer. FIG. 8B. Ovarian cancer. FIG. 8C. Prostate cancer. FIG. 8D. Breast cancer. FIG. 8E. Non-small cell lung cancer. FIG. 8F. Small cell lung cancer. FIG. 8G. Pancreatic cancer. FIG. 8H. Colon cancer. FIG. 8I. Non-Hodgkin lymphoma. FIG. 8J. Melanoma. The approximate location of unreactive (at background) albumin (Ab) is labeled for comparison. Approximately 180 non-cancer patient sera were analyzed in parallel without evidence of proteins indicative of specific transcript variants for comparison as positive controls.

FIGS. 9A and 9B show analytical gel electrophoresis and immunoblots of patient sera. FIG. 9A. Sera from a patient with non-small cell lung cancer contains a 54 kDa, isoelectric point pH 5.1 transcript variant (arrow). FIG. 9B. Sera from a patient with small cell lung cancer contains a 52 kDa, isoelectric point 4.3 transcript variant (arrow). The reference spots to the right, MW 52 kDa and isoelectric point pH 4.1 are α1-antitrypsin inhibitor. Albumin and other serum proteins are unreactive.

Figure 10:
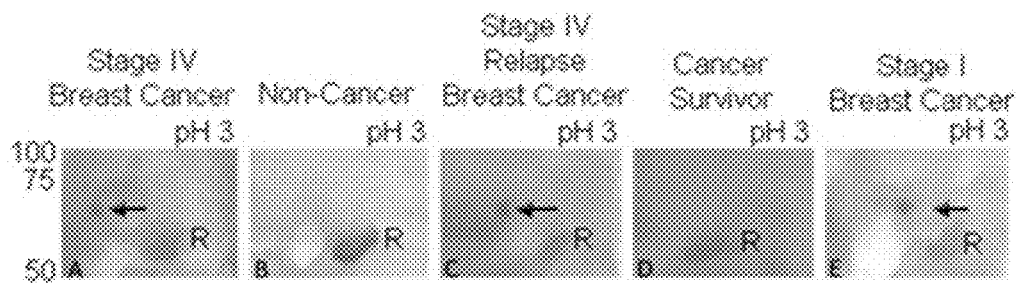
FIG. 10 shows 2-D gel electrophoretic separations and detection of ENOX2 transcript variants specific for breast cancer by western blotting of patient sera. Arrow=66 to 68 kDa breast cancer specific transcript variant. R=52 kDa, isoelectric point pH 4.1 $\alpha$-fetuin reference spot.

FIG. 10 shows 2-D gel electrophoretic separations and detection of ENOX2 transcript variants specific for breast cancer by western blotting of patient sera. Arrow=66 to 68 kDa breast cancer specific transcript variant. R=52 kDa, isoelectric point pH 4.1 α-fetuin reference spot.

Sera from individual patients with various forms of cancer were analyzed by 2-D gel electrophoresis and immunoblotting to assign each of the ENOX2 isoforms of FIG. 7 to a cancer of a particular tissue of origin (see Table 3). ENOX2 transcript variants with apparent molecular weights in the range of 64-69 kDa. pH in the range of 4.2-4.9 are associated with breast cancer. ENOX2 transcript variants of 52-53 kDa, pH 4.1-4.6 is associated with small cell lung cancer. An ENOX2 transcript variant of 54-56 kDa, pH 4.6-5.3 is associated with non-small cell lung cancer. Two ENOX2 transcript variants of about 72-90 kDa and 37-47 kDa, isoelectric point pH 3.7-5.0 for both, characterize ovarian cancer. ENOX2 transcript variants of 71-88 kDa, pH 5.1-6.5 are associated with prostate cancer. An ENOX2 transcript variant of about 90-100 kDa, pH 4.2-5.4 signals cervical cancer. Three ENOX2 transcript variants of about 80-96 kDa, pH 4.4-5.4; 50-65 kDa, pH 4.2-5.3; and 33-46 kDa, pH 3.8-5.2 are characteristic of colon cancer. Where a patient is suspected of having cancer, the 2D gel electrophoresis/immunological analysis of a biological sample, advantageously a serum sample, will reveal both cancer presence and organ site with the present invention.

The protein sequence of ENOX2 exhibits similarity with the two reference proteins alpha-fetuin and serrotransferrin reactive with the pan ENOX2 scFv recombinant antibody. Regions of similarity are restricted to a 7 amino acid sequence (underlined) adjacent in ENOX2 to the E394EMTE398 quinone inhibitor-binding site, which serves as the antigen sequence to which the specific scFv antibodies bind.

| | | |
|---|---|---|
| ENOX2 | EEMTET<u>KETEESA</u>LVS | (SEQ ID NO: 1) underlined AA 399-406 |
| Alpha-fetuin | GTDCVA<u>KEATEAA</u>KCN | (SEQ ID NO: 2) underlined AA 210-216 |
| Serro-transferrin | CLDGTR<u>KPVEEYA</u>NCH | (SEQ ID NO: 3) underlined AA 588-595 |

A. Sample Preparation
1. Prepare/thaw re-hydration solution (−20, 1.5 mL tube labeled RB).
   a. Add 1% Dithiothreitol (DTT) to solution before use (0.01 g/1.0 mL).
2. Add 120 μL of Rehydration Buffer to a 1.7 ml tube.
3. Add 30 μL of sera to tube.
4. Vortex solution until fully mixed.
5. Remove Immobiline DryStrips from freezer (−20° C., pH 3-10) and allow strips to equilibrate to RT for 5 minutes.
   a. Do not leave strips at RT for more than 10 minutes.
6. Record ID# from strip.
7. Load 130 μL of sample to tray per 7 cm DryStrip. Ensure tray is level.
8. Place Dry Strips gel-side down over sample.
9. Ensure sample is evenly spread throughout strip by carefully lifting strip in and out of sample a few times if needed.
10. If samples are concentrated in one region of the strip, redistribute sample by pipetting.
11. Remove air bubbles by gently pressing down on Dry Strip with pipette tip.
12. Place lid on tray and place tray in plastic bag with ddi-H2O soaked paper towels.
13. Seal bag.
14. Allow sample to re-hydrate overnight at RT on a level surface allowing strips to absorb sample for 12-24 hours.

B. Isoelectric Focusing (First Dimension)
1. Turn on IPGphor (ensure proper startup of machine).
2. Place strips on Manifold focusing tray as follows:
   a. Gel side up.
   b. positive (acidic) end towards back.
   c. Strips are aligned.
   d. Between metal strips (so electrodes fit and touch metal strip)
3. Obtain 2 Paper Wicks per strip.
4. Wet wicks with 150 μL di-H2O per wick.
5. Place wicks over anodic and cathodic ends of gel (approx. 0.3 cm).
6. Place electrodes on wicks, but away from gel (be sure prong is on metal plate), and lock in place.
7. Cover strips with DryStrip Cover fluid.
   a. Fill strips entire lane with oil.
   b. Ensure strips are fully covered.
8. Close lid.
9. IEF run with IPGphor II.
   a. Maximum amperage: 50 μAmps.
   b. Temperature: 20° C.
   c. Ensure correct assembly by checking initial voltage.
   d. As needed, pause run and replace wicks, continue run until dye front disappears.

Run Parameters:

| | Step | Voltage | Time/Vhrs |
|---|---|---|---|
| 7 cm Strip pH 3-10 (Run #1) | 1-Stp. | 250 V | 250 Vhrs, |
| | 2-Stp. | 500 V | 500 Vhrs. |
| | 3-Stp. | 1000 V | 1000 Vhrs. |
| | 4-Grd. | 4000 V | 3 hrs. |
| | 5-Stp. | 4000 V | 25,000 Vhrs. |
| | 6-Stp. | 500 V | Hold |

C. Prepare SDS-Page Gels (for Second Dimension)
1. Prior to use, wash and scrub plates very well in soap and hot water.
2. Rinse in di-H2O.
3. Leave the plates to air dry or wipe with ethanol-soaked Kimwipes.
4. Order plates in Protean-plus Multi-Gel casting Chamber (Bio-Rad) as per manual (with a spacer between each plate and block).
5. Ensure screws are fully tightened.
6. Add gel solution.
7. Stop pouring when gel is about 1-1.5 cm from top of glass plates.
8. Gently overlay gels with ethanol.
9. Cover with Saran Wrap.
10. Allow gels to polymerize for at least one hour (best if overnight).

D. Equilibration (First Dimension)
1. Remove strips from tray and place on Kimwipe to remove excess oil.
   1. Place strips gel side up on Kimwipe.
   2. Overlay strips with a second Kimwipe and gently blot to remove oil.
2. Place strips in equilibration plate gel side up; freeze or equilibrate.
   1. Freeze: Wrap plate in plastic wrap, store at −80° C.
      a. Thaw strips prior to equilibration (clear when thawed).
   2. Equilibrate: continue to next step.
3. Cover strips with equilibration buffer, about 1.5 mL per strip.
4. Heat up Agarose until it is liquefied.
5. Shake 20 min at RT.

E. SDS-PAGE (Second Dimension)
1. Prepare left (pH 10 side) markers by adding 8 μL of standards on Whatman 3 MM chromatography paper cut to about 3 cm×0.75 cm. Standards should be added to bottom of paper, about 1 cm high.
2. Prepare right (pH 3 side) markers by adding 8 μL of standards on Whatman 3 MM chromatography paper cut to approximately 3 cm×0.0.75. Standards should be added to bottom of paper, about 1 cm high.
3. Pour off Equilibration Buffer.
4. Cover strips in SDS Running buffer to rinse away excess Equilibration Buffer
5. Remove SDS Running buffer from strips.
6. Repeat SDS Running buffer rinse.
7. Carefully place strips gel side out on back plate of SDS-PAGE gel.

8. Overlay strips with 1% low melting agarose once it has cooled enough to touch skin.
   1. Ensure no air bubbles have formed under the gel.
   2. Use ruler to tap gel and remove air bubbles.
9. Insert marker's next to appropriate end of IEF strip, ensuring marker is flush to the gel on the strip.
10. Allow polymerization of agarose.
11. Continue for each strip to be loaded in 2nd dimension.
12. Place gels in Dodeca tank, HINGED SIDE DOWN
13. After all gels have been put in tank, ensure gels are covered in entirety by SDS running buffer.
14. 2nd dimension run is done at 13° C.
   1. 250 V.
   2. 1-1.5 hour (allow gel to run until gel front approaches tubing in lid of tank).
F. Protein Transfer (for Western Blot)
1. Remove gel from Dodeca tank.
2. Cut gel to desired size.
3. Fill tray (large enough to fit gel) with transfer buffer.
4. Place sponges in transblot cell—2 sponges per gel.
5. Fill tank with transfer buffer to allow sponges to saturate with transfer buffer.
6. Soak pre-cut transfer membrane.
7. Assemble transfer cassette as follows.
   1. Black side down.
   2. Sponge soaked in transfer buffer.
   3. Filter paper.
   4. Gel.
   5. Nitrocellulose membrane—once placed on gel do not move membrane.
   6. Filter Paper.
   7. Sponge.
8. Ensure all air bubbles have been removed between gel and membrane.
9. Place tray in transblot tank, black side (gel side) of tray to black tank side.
10. Transfer at 4° C. and following conditions (transfer can be done in an ice bath if needed).
    1. 90 V for 50 minutes.
    2. Membrane can be left in tank overnight at 4° C. after transfer.
G. Immunological Analysis for Western Blot Using scFv with S-Tag Linked to Alkaline Phosphatase or Alkaline Phosphatase Linked Anti S-Tag so as to Amplify Signal
1. Remove membrane from transfer.
2. Rinse membrane in 1% milk (enough to cover membrane) and block, 10 minutes, RT.
3. Prepare antibody solution (According to Titer instructions on Ab).
4. Remove blocking solution (save at 4° C.).
5. Place membrane into container with antibody solution.
6. Incubate at 4° C. overnight (usually 8-12 hours).
H. Development of Western Blot and Scanning
1. Remove 1° antibody.
2. Wash membrane 4 times.
   1. Cover membrane with TBST.
   2. Gently shake at RT for 5 minutes.
3. Cover membrane with Western Blue.
4. Allow to develop until reference spots reach maximum intensity.
5. Stop develop by rinsing with di-H2O.
6. Dry membrane.
7. Scan membrane.

Solutions Used for First Dimension
I. Rehydration Buffer pH 7 (25 mL):

| Chemical | Amount Added | Molar Mass (g/mol) | Final Value |
| --- | --- | --- | --- |
| Urea | 10.51 g | 60.06 | 7M |
| Thiourea | 3.81 g | 76.12 | 2M |
| CHAPS | 0.5 g | 614.88 | 2% |
| asb-14 | 0.125 g | 434.68 | 0.5% |
| 40% Ampholytes | 330 μL | NA | 0.5% |
| IPG Buffer | 125 μL | N/A | 0.5% |
| ddi-H2O | To 25 μL | 18.02 | N/A |
| BromaplsenalBlue | 3 mg | 669.96 | 0.012% |

Dissolve Urea in minimal ddi-H$_2$O (do not beat over 30° C.).
Dissolve Thiourea in Urea/ ddi-H$_2$O solution, and than add remaining chemicals.
Q.S. with ddi-H$_2$O 25 mL and aliquot to 1 ml. tubes and store at −80° C.
Add 1% DTT-10 mg (0.01 g) before use.

Solutions Used for Second Dimension
Tris Buffer (1.5 M, pH 8.8) (1 L):

| Chemical | Amount Added | Molar Mass (g/mol) | Final Value |
| --- | --- | --- | --- |
| Trizma | 181.65 g | 121.14 | 1.5M |
| HCl | pH to 8.8 | 36.46 | N/A |
| ddi-H$_2$O | To 1 L | 18.02 | N/A |

Dissolve Trizma in 750 mL ddi-H$_2$O and adjust pH to 8.8 with HCL
Q.S. to final volume of 1 L with ddi-H$_2$O and store at 4° C.

Equilibration Buffer (400 mL):

| Chemical | Amount Added | Molar Mass (g/mol) | Final Value |
| --- | --- | --- | --- |
| Tris-Buffer (1.5M, pH 8.8) | 134 mL | N/A | 0.5M |
| Urea | 144.14 g | 60.06 | 6M |
| Glycerol | 120 mL (150 g.) | 92.09 | 30% |
| SDS | 10 g | 288.38 | 2.5% |
| ddi-H$_2$O | To 400 ml | 18.02 | N/A |
| Bromophenol Blue | Trace Amount | 669.96 | N/A |

Q.S. to final volume of 4 L with ddi-H$_2$O
Add Bromophenol Blue (add with pipette trip to give trace of blue).
Aliquot be 15 mL tubes and store −20° C.

Acrylamide Gel (20 cm×20 cm; 1-mm Thick)

| Gel % | # gels | Tris Buffer 1.5M, pH 8.8 (mL) | 30% Acrylamide (mL) | ddi-H$_2$O (mL) | 10% APS (mL) | TEMED (mL) |
| --- | --- | --- | --- | --- | --- | --- |
| 10 | 6 | 100 | 133.33 | 166.67 | 4 | 0.4 |
|  | 8 | 125 | 166.67 | 208.33 | 5 | 0.5 |
|  | 10 | 150 | 200 | 250 | 6 | 0.6 |
|  | 12 | 175 | 233.33 | 291.67 | 7 | 0.7 |

Formulations for Protean II gels.

10% Alkaline Phosphatase Substrate (APS)

| Chemical | Amount Added | Molar Mass (g/mol) | Final Value |
| --- | --- | --- | --- |
| APS | 2 g | 228.18 | 10% |
| ddi-H$_2$O | To 20 mL | 18.02 | N/A |

Q.S. to final volume of 20 mL with ddi-H$_2$O.

Agarose Solution (1%):

| Chemical | Amount Added | Molar Mass (g/mol) | Final Value |
|---|---|---|---|
| Agarose | 1.5 g | N/A | 1% |
| SDS-Running Buffer | 150 mL | N/A | N/A |
| Bromophenol Blue | Trace amount | 669.96 | N/A |

Combine agarose and SDS-Run Buffer.
Microwave to heat and dissolve.
Add Bromophenol Blue (add with pipette tip to give trace of blue).

10×SDS Running Buffer (4 L):

| Chemical | Amount Added | Molar Mass (g/mol) | Final Value |
|---|---|---|---|
| Trizma | 121.2 g | 121.14 | 0.25M |
| Glycine | 576 g | 75.07 | 1.92M |
| SDS | 40 g | 288.38 | 1% |
| ddi-$H_2O$ | To 4 L | 18.02 | N/A |

Q.S. to final volume of 4 L with ddi-$H_2O$.

Solutions for Western Blot
Western Transfer Buffer (4 L):

| Chemical | Amount Added | Molar Mass (g/mol) | Final Value |
|---|---|---|---|
| Trizma | 12.12 g | 121.14 | 0.025M |
| Glycine | 57.6 g | 75.07 | 0.192M |
| Methanol | 480 mL | 32.04 | 0.12% |
| SDS | 3 g | 288.38 | .075% |
| di-$H_2O$ | To 4 L | 18.02 | N/A |

Q.S. to final volume of 4 L with di-$H_2O$.

Blocking Buffer (5% BSA)

| Chemical | Mass | Molar Mass (g/mol) | Final Value |
|---|---|---|---|
| BSA | 5 g | 66500 | 5% |
| $N_3Na$ | 0.2 g | 65.01 | 0.2% |
| TBST | To 100 mL | 18.02 | N/A |

Q.S. to final volume of 100 mL with TBST.

10× Tris Buffered Saline with Tween-20 (TBST) (4 L)

| Chemical | Amount Added | Molar Mass (g/mol) | Final Value |
|---|---|---|---|
| Trizma | 48.4 g | 121.14 | 100 mM |
| NaCl | 350.6 g | 58.44 | 1.5M |
| Tween 20 | 20.6 g | 1227.54 | 0.5% |
| HCl | pH to 7.5 | 36.46 | N/A |
| ddi-$H_2O$ | To 4 L | 18.02 | N/A |

Add Trizma and NaCl to 3.5 L ddi-$H_2O$.
pH to 7.5 by HCl
Add Tween 20.
Q.S. to 4 L with ddi-$H_2O$.

Method 3—2-D Gel Electrophoresis Western Blot Early Detection Protocol.

Serum was prepared from 5 ml of blood collected by venipuncture (with tourniquet) in standard B & D 13×100 (7 ml) vacutainer clot tubes (or equivalent) with or without hemoguard closure. After approximately 30 minutes at room temperature to allow for clotting, the clot was pelleted by centrifugation for 5 to 10 minutes at 2,500 to 3,000 rpm. Clot-free serum was decanted into a clean tube, labeled and analyzed fresh or stored frozen.

For western blot analysis, 30 μL of sera was added to 120 μL of Rehydration Buffer (7M urea, 2 M thiourea, 2% (w/v) CHAPS [(3-[(3-cholamidopropyl)dimethylammonio]-1-propane-sulfonate), a nondenaturing zwitterionic detergent], 0.5% (w/v) ASB-14 (amidosulfobetaine-14, a zwitterionic detergent), 0.5% (v/v) ampholytes pH 3-10 (Bio-Rad), 0.5% (v/v) immobilized pH gradient (IPG) buffer pH 3-10 (Amersham-Pharmacia Biotech) and 65 mM dithiothreitol). The samples were quickly vortexed to mix sera with Rehydration Buffer. Four to six mg of protein were loaded for analysis. The samples were electrophoresed in the first dimension by using a commercial flatbed electrophoresis system (Ettan IPGphor 3, Amersham-Pharmacia Biotech) with IPG dry strips (Amersham). A linear pH range of 3 to 10 on 7 cm IPG strips was used. The IPG strips were rehydrated with the samples overnight at room temperature. The strips were then focused at 50 mA per strip and at increasing voltage of 250 V for 250 Vhrs, 500 V for 500 Vhrs, 1,000 V for 1,000 Vhrs and 4,000 V for 3 hours. The samples were then focused at a constant 4,000 V for 28,000 Volt-hours. After isoelectric focusing, the IPG strips were re-equilibrated for 20 minutes in 2.5% (w/v) SDS, 6 M urea, 30% (v/v) glycerol, 100 mM Tris-HCl (pH 8.8). The strips were placed onto linear SDS-PAGE gels (10% (w/v) polyacrylamide) and electrophoresed at a constant 250 V for 75 minutes. The samples were then transferred to nitrocellulose membranes by electroblotting using the Bio-Rad Trans-Blot Electrophoretic Transfer Cell. The membranes were blocked using milk protein (1% low fat dry milk) at room temperature for 10 minutes. Detection was with recombinant anti-ENOX2 single chain variable region of antibody (scFv) that was alkaline phosphatase-linked overnight at 4° C. After washing, detection was performed with Western Blue nitrotetrazolium (NBT) substrate (Promega, Madison, Wis.; Cat. No. 53841) at room temperature. Images were scanned and processed using Adobe Photoshop. Quantitation utilized an algorithm developed for this purpose. Reactive proteins appeared reddish blue. For interpretative purposes, the blots were divided into quadrants I-IV with unreactive serum albumin at the center (FIG. 7).

EXAMPLES

Example 1

Figure 1:
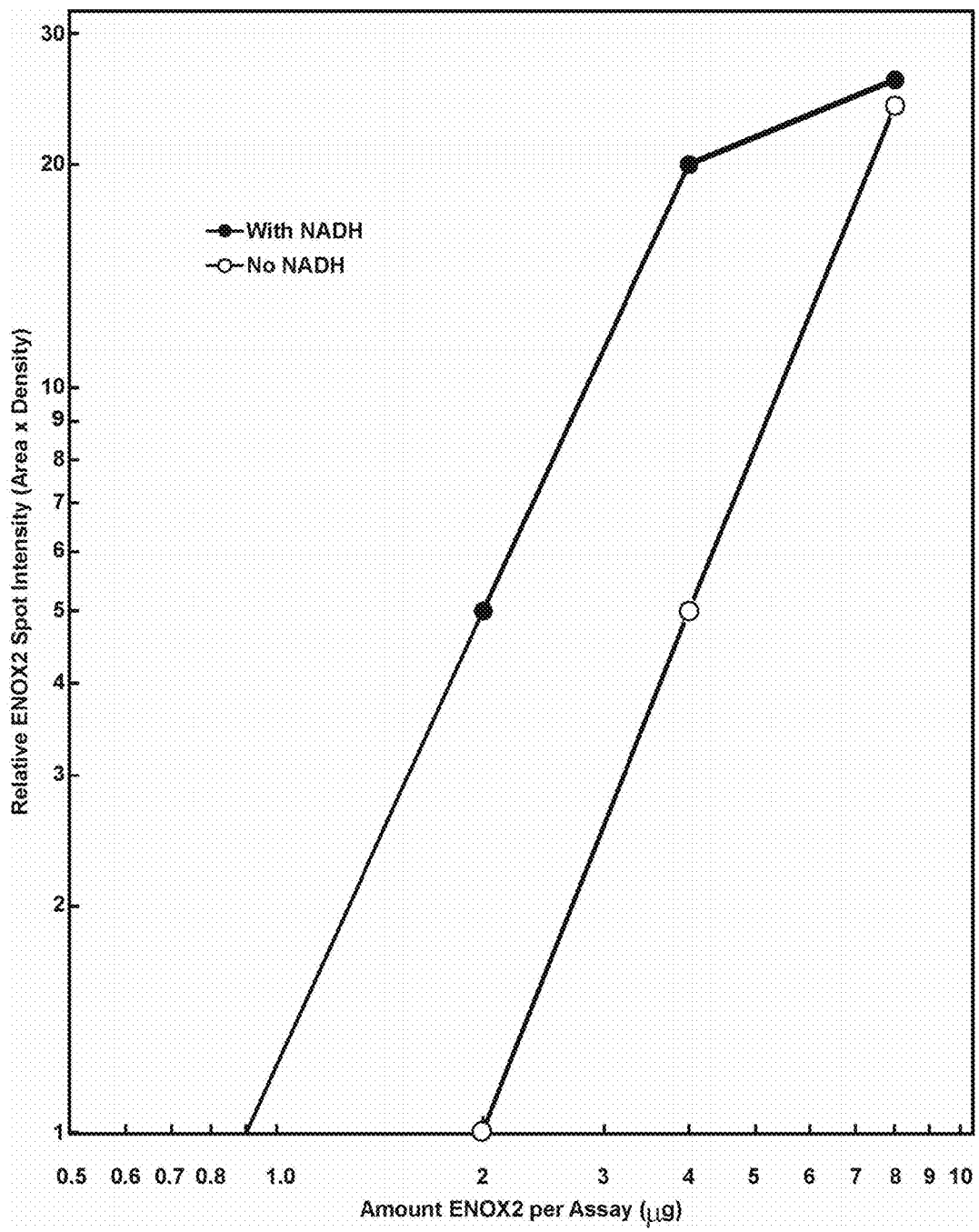
FIG. 1 is a graph that demonstrates a two-fold increase in spot size and density of different amounts of ENOX2 in the assay as determined by 2-D gel electrophoresis/western blot analysis comparing incubation in the presence of 15 µM NADH in the assay compared to no NADH.

Two-fold increase in spot size and density of different amounts of ENOX2 in the assay as determined by 2-D gel electrophoresis/western blot analysis comparing incubation in the presence of 15 μM NADH in the assay compared to no NADH (FIG. 1).

Example 2

Analyses of sera from 1,626 cancer patients with confirmed diagnoses of cancer (Table 1, repeated from the Summary of the Invention) showing non-lapping patterns of number of transcript variants (protein 1 to protein 3), molecular weights and isoelectric points that distinguish 26 different cancers and 20 different tissues of origin.

Table 1, repeated from the Summary of the Invention: Ranges for Molecular Weight (MW) and Isoelectric Point (Pi) Determined for Sera of Patients Diagnosed with 24 Different Cancers Representing 20 Different Tissues of Origin

| Cancers | N | Protein 1 MW (kDa) | Protein 1 Pi (pH) | Protein 2 MW (kDa) | Protein 2 Pi (pH) | Protein 3 MW (kDa) | Protein 3 Pi (pH) |
|---|---|---|---|---|---|---|---|
| Bladder | 37 | 63-66 | 4.2-5.6[1] | 42-48 | 4.1-4.8[1] | | |
| *Blood Cell (Total) | (117) | 34-47 | 3.5-4.6 | | | | |
| Breast | 682 | 64-69 | 4.2-4.9 | | | | |
| Cervical | 47 | 90-100 | 4.2-5.4 | | | | |
| Colorectal | 125 | 80-96 | 4.4-5.4 | 50-65 | 4.2-5.3 | 33-46 | 3.8-5.2 |
| Esophageal | 26 | 42-47 | 4.6-5.2 | | | | |
| Gastric | 26 | 120-188 | 4.7-5.5 | 50-62 | 4.5-5.6 | 45-53 | 2.4-3.6 |
| Hepatocellular | 31 | 58-70 | 4.5-5.0 | 34-40 | 4.1-5.2 | | |
| Leukemias | 36 | 34-45 | 3.5-4.5 | | | | |
| *Lung, Non-Small Cell | 55 | 53 | 4.7-5.3 | | | | |
| **Lung, Non-Small Cell | 270 | 54-56 | 4.6-5.3 | | | | |
| Lung, Small Cell | 27 | 52-53 | 4.1-4.6 | | | | |
| Lymphomas | 56 | 43-45 | 3.5-4.5 | | | | |
| Melanoma | 51 | 37-41 | 4.6-5.3 | | | | |
| Mesothelioma | 27 | 60-68 | 3.8-4.1 | 38-44 | 3.8-4.6 | | |
| Myelomas | 25 | 40-45 | 3.9-4.6 | | | | |
| Ovarian | 115 | 72-90 | 3.7-5.0 | 37-47 | 3.7-5.0 | | |
| Pancreatic | 75 | 48-51 | 3.9-5.4 | | | | |
| Prostate | 361 | 71-88 | 5.1-6.5 | | | | |
| Renal Cell (Kidney) | 31 | 69-73 | 4.7-5.4 | 54-61 | 4.1-5.2 | 38-43 | 3.7-4.3 |
| Sarcoma | 29 | 50-55 | 5.2-5.6 | 37-45 | 4.3-4.9 | | |
| Squamous Cell | 51 | 57-68 | 5.0-5.4 | | | | |
| Testicular Germ Cell | 25 | 61-62 | 5.0-5.4 | 40-45 | 4.4-4.7 | | |
| Thyroid Follicular | 25 | 48-56 | 4.7-5.1 | 37-42 | 4.5-5.2 | | |
| Thyroid Papillary | 27 | 56-67 | 4.5-5.0 | 37-44 | 3.2-3.6 | | |
| ***Uterine (Endometrial) | 26 | 63-66 | 4.2-4.9[2] | 41-48 | 4.4-5.6[2] | | |
| **Uterine (Endometrial) | 57 | 67-71 | 4.2-5.1 | 41-48 | 3.7-5.4 | | |
| Total | 2460 | | | | | | |

*Blood cell cancers include lymphomas, leukemias and myelomas already represented in the totals.
**Non-Small Cell Lung cancers are in two subsets to avoid molecular weight overlap with small cell lung cancer.
***Uterine cancers are in two subsets based on molecular weight to avoid overlap with bladder cancer (see footnotes 1 and 2).
1. Isoelectric point pH of Protein 1 ≥ Protein 2.
2. Isoelectric point pH of Protein 1 < Protein 2.

Example 3

The ONCOblot test correctly identified cancers as to tissue of origin with both state 0 and Stage I cancers (Table 3). Often referred to as cancer in situ, with stage 0 and stage I cancers, the disease has not spread beyond the tissue of origin. Thus, the ONCOblot Cancer Test signals cancer earlier than Circulating Tumor Cell tests that detect only cancer cells in the blood.

TABLE 3

The tissue of origin stage 0 and stage I cancers analyzed

| Stage 0 Cancers | n | Stage I Cancers | n |
|---|---|---|---|
| Bladder | 2 | Bladder | 1 |
| Blood Cell | 3 | Blood Cell | 2 |
| Breast | 6 | Breast | 16 |
| Cervix | 3 | Colorectal | 5 |
| Hepatocellular (Ampullary) | 1 | Lung | 1 |
| Lung | 1 | | |
| Melanoma | 1 | | |
| Renal Cell | 2 | | |
| Squamous Cell (Vulvar) | 2 | | |
| Uterine | 1 | | |

Example 4

A 64 year old male was followed longitudinally for 16 years by using archived serum samples. The starting PSA was 0.8 ng/mL. No clinical symptoms were recorded until year 16 when prostate cancer was confirmed by biopsy. ENOX2 was first detected in year 8 with a PSA of 4 ng/ml 8 years in advance of clinical symptoms.

Example 5

Malignant mesothelioma is an aggressive, almost uniformly fatal cancer caused primarily by exposure to asbestos. Sequential serum samples collected from asbestos-exposed individuals prior to the development of frank mesothelioma were assayed for ENOX2 presence by 2-D gel-immunoblot analysis to determine how long in advance of clinical symptoms mesothelioma-specific transcript variants could be detected. Two mesothelioma-specific transcript variants were detected in the sera of asbestos-exposed individuals 4 to 10 years prior to clinical diagnosis of malignant mesothelioma (average 6.2 years). Either one or both ENOX2 protein transcript variants indicative of malignant mesothelioma were absent in 14 of 15 subjects diagnosed with benign pleural plaques either with or without accompanying asbestosis.

Example 6

Analysis of patient sera with cancer of unknown primary (CUP). The 2-D gel from a patient with cancer where the primary tumor was unknown revealed the presence of 80 and 42.5 kDa, both with transcript variants of isoelectric points of pH 4.2 and 4.1 to indicate that the primary cancer was ovarian cancer, which was confirmed later by biopsy.

Example 7

Successful validation and quantitation of ENOX2 presence in 1,587 ONCOblot analyses comparing 20 different tissues of origin (Table 1).

Example 8

Early detection of cancer in a healthy population of young adults in advance of clinical symptoms. Sera from 100 subjects (50 male and 50 female) between the ages of 20 and 39 years were analyzed for ENOX2 presence by the technology described herein. In the age group 20-29 years, none of the 25 females and only one (colorectal) of the 25 males exhibited ENOX2 proteins indicative of cancer presence. Similarly, in the age group 30-39 years, one (blood cell) of the 25 females and one (prostate) of the 25 males exhibited ENOX2 proteins. Therefore, the overall incidence of ENOX2 presence within all 100 serum samples was 3%. The overall incidence of newly diagnoses cancers within a population of men and women between 20 and 29 years old is approximately 2% (Howlander et al. SEER Cancer Statistics Review, 1975-2012, National Cancer Institute, Bethesda, Md.).

Method 4—Generation of Functionalized Recombinant Antibody with Protein Disulfide-Thiol Interchange Functional Motif Represented in Linker.

To further enhance the affinity and specificity of the binding of the recombinant antibody to ENOX2 on western blots a linker was designed to specifically mimic the protein disulfide-thiol interchange functional motif of the ENOX2 family of proteins.

Monoclonal antibody generated against ENOX2 NADH oxidase tumor cell specific was produced in sp-2 myeloma cells; however, the monoclonal antibody slowed the growth of sp-2 myeloma cells that were used for fusion with spleen cells after 72 hours. This phenomenon made it difficult to produce antibody in quantity. To overcome this problem, the coding sequences of the antigen-binding variable region of the heavy chain and the light chain (Fv region) of the antibody cDNA were cloned and linked into one chimeric gene, upstream of the S-tag coding sequence. The Fv portion of an antibody, consisting of variable heavy (VH) and variable light (VL) domains, can maintain the binding specificity and affinity of the original antibody (Glockshuber et al. 1990. *Biochemistry* 29:1262-1367).

For a recombinant antibody, cDNAs encoding the variable regions of immunoglobulin heavy chain (VH) and light chain (VI), were cloned using degenerative primers. Mammalian immunoglobulins of light and heavy chain contain conserved regions adjacent to the hypervariable complementary defining regions (CDRs). Degenerate oligoprimer sets allow these regions to be amplified using PCR (Jones et al. 1991. *Bio/Technology* 9:88-89; Daugherty et al. 1991. *Nucleic Acids Research* 19:2471-2476). Recombinant DNA techniques have facilitated the stabilization of variable fragments by covalently linking the two fragments by a polypeptide linker (Huston et al. 1988. *Proc. Natl. Acad. Sci. USA* 85:5879-5883). Either VL or VH can provide the NH2-terminal domain of the single chain variable fragment (scFv). The linker should be designed to resist proteolysis and to minimize protein aggregation. Linker length and sequences contribute and control flexibility and interaction with scFv and antigen. The preferred linker was uniquely comprised as a functional linker between heavy and light chain portions of the ScFv fusion protein comprised primarily of amino acids with small side chains (Gly/Ser) containing, in addition, two cysteine residues (C) spaced as either CXXXXC or CXXXXXC; that forms interchain disulfide bonds with the protein disulfide-thiol interchange functional motif of ENOX2.

Total RNA was isolated from the hybridoma cells producing ENOX2-specific monoclonal antibodies by the following procedure modified from Chomczynski et al. (1987) *Anal. Biochem.* 162:156-159 and Gough (1988) *Anal. Biochem* 176:93-95. Cells were harvested from medium and pelleted by centrifugation at 450×g for 10 minutes. Pellets were gently resuspended with 10 volumes of ice cold PBS and centrifuged again. The supernatant was discarded and cells were resuspended with an equal volume of PBS. Denaturing solution (0.36 ml of 2-mercaptoethanol/50 ml of guanidinium stock solution-4M guanidinium thiocyanate, 25 mM sodium citrate, pH 7.0, 0.5% sarkosyl) 10 ml per 1 g of cell pellet was added prior to use and mixed gently. Sodium acetate (pH 4.0, 1 ml of 2M), 10 ml of phenol saturated water and 2 ml of chloroform: isoamyl alcohol (24:1) mixtures were sequentially added after each addition. The solution was mixed thoroughly by inversion. The solution was vigorously shaken for 10 seconds, chilled on ice for 15 minutes and then centrifuged 12,000×g for 30 minutes. The supernatant was transferred and an equal volume of 2-propanol was added and placed at −20° C. overnight to precipitate the RNA. The RNA was pelleted for 15 minutes at 12,000×g, and the pellet was resuspended with 2-3 ml of denaturing solution and 2 volumes of ethanol. The solution was placed at −20° C. for 2 hours, and then centrifuged at 12,000×g for 15 minutes. The RNA pellet was washed with 70% ethanol and then 100% ethanol. The pellet was resuspended with RNase-free water (DEPC-treated water) after centrifugation at 12,000×g for 5 minutes. The amount of isolated RNA was measured spectrophotometrically and calculated from the absorbance at 280 nm and 260 nm.

A poly(A)mRNA isolation kit was purchased from Stratagene. Total RNA was applied to an oligo(dT) cellulose column after heating the total RNA at 65° C. for 5 minutes. Before applying, the RNA samples were mixed with 500 μL of 10× sample buffer (10 mM Tris-HCl, pH 7.5, 1 mM EDTA, 5 M NaCl). The RNA samples were pushed through the column at a rate of 1 drop every 2 seconds. The eluates were pooled and reapplied to the column and purified again. Preheated elution buffer (65° C.) was applied, and mRNA was eluted and collected in 1.5 ml of centrifuge tubes on ice. The amount of mRNA was determined at OD260 (1 OD unit=40 μg of RNA). The amounts of total RNA and mRNA obtained from 4×10 e 8 cells were 1328 μg and 28 μg, respectively.

Next, mRNA (1-2 μg) dissolved in DEPC-treated water was used for cDNA synthesis. mRNA isolated on three different dates was pooled for first-strand cDNA synthesis. The cDNA synthesis kit was purchased from Pharmacia Biotech. The mRNA (1.5 μg/5 μL of DEPC-treated water) was heated at 65° C. for 10 minutes and cooled immediately on ice. The primed first strand mix containing Murine Leukemia Virus (MuLV) reverse transcriptase (11 μL) and appropriate buffers for the reaction were mixed with the mRNA sample. DTT solution (1 μL of 0.1 M) and RNase-free water (16 μL) also were added to the solution. The mixture was incubated for 1 hour at 37° C.

Degenerate primers for light chain and heavy chain (Novagen, Madison, Wis.) were used for PCR. PCR synthesis was carried out in 100 μL reaction volumes in 0.5 ml microcentrifuge tubes by using Robocycler (Stratagene, La Jolla, Calif.). All PCR syntheses included 2 μL of sense and anti-sense primers (20 picomoles/μL), 1 μL of first-strand cDNA as a template, 2 μL of 10 mM of dNTPs, 1 μl of Vent polymerase (2 units/μL), 10 μL of 10×PCR buffer (100 mM Tris-HCl, pH 8.8 at 25° C., 500 mM KCl, 15 mM MgCl2, 1% Triton X-100), 82 μL of H2O. Triton X-100 is t-octyl-phenoxypolyethoxyethanol. All PCR profiles consisted of 1 min of denaturation at 94° C., 1 minute of annealing at 55° C., and 1 minute of extension at 72° C. This sequence was repeated 30 times with a 6-minute extension at 72° C. in the final cycle. PCR products were purified with QIAEX II gel extraction kit from Qiagen, Valencia, Calif. PCR amplification products for heavy and light chain coding sequences were analyzed by agarose gel electrophoresis and were about 340 base pair (bp) long and 325 bp long, respectively.

Total RNA or DNA was analyzed by agarose gel electrophoresis (1% agarose gels). Agarose (0.5 g in 50 ml of Tris-acetate-EDTA (TAE) buffer, 40 mM Tris-acetate, 1 mM EDTA) was heated for 2 minutes in a microwave to melt and evenly disperse the agarose. The solution was cooled at room temperature, and ethidium bromide (0.5 μg/ml) was added and poured into the apparatus. Each sample was mixed with 6× gel loading buffer (0.25% bromophenol blue, 0.25% xylene cyanol FF, 40% (w/v) sucrose in water). TAE buffer was used as the running buffer. Voltage (10 v/cm) was applied for 60-90 minutes.

According to the proper size for heavy and light chain cDNAs, the bands were excised from the gels under UV illumination, and excised gels were placed in 1 ml syringes fitted with 18-gauge needles. Gels were crushed to a 1.5 ml Eppendorf tube. The barrel of each syringe was washed with 200 µL buffer-saturated phenol (pH 7.9±0.2). The mixture was thoroughly centrifuged and frozen at −70° C. for 10 minutes. The mixture was centrifuged for 5 minutes, and the top aqueous phase was transferred to a new tube. The aqueous phase was extracted again with phenol/chloroform (1:1). After centrifuging for 5 minutes, the top aqueous phase was transferred to a clean tube, and chloroform extraction was performed. Sodium acetate (10 volumes of 3 M) and 2.5 volumes of ice-cold ethanol were added to the top aqueous phase to precipitate DNA at −20° C. overnight.

Purified heavy and light chain cDNAs were ligated into plasmid pSTBlue-1 vector and transfected into NovaBlue competent cells (Stratagene). Colonies containing heavy and light chain DNAs were screened by blue and white colony selection and confirmed by PCR analysis. Heavy and light chain DNAs were isolated and sequenced using standard techniques.

PCR amplification and the assembly of single scFv gene was according to Davis et al. (1991) *Bio/Technology* 9:165-169. Plasmid pSTBlue-1 carrying VH and VL genes were combined with all four oligonucleotide primers in a single PCR synthesis. Following first PCR synthesis, one tenth of the first PCR product was removed and added to a second PCR reaction mixture containing only the primer a (VH sense primer) and primer d (VL Antisense primer). The product of the second PCR synthesis yielded single scFv gene. The single scFv gene was ligated to plasmid pT-Adv (Clontech, Palo Alto, Calif.). pT-Adv carrying scFv gene was used for DNA sequencing.

The complete functionalized scFv gene was assembled from the VH, VL and linker sequences to yield an scFv cDNA with a high degree of efficacy and sensitivity.

Total RNA or DNA was analyzed by agarose gel electrophoresis (1% agarose gels). Agarose (0.5 g in 50 ml of TAE buffer, 40 mM Tris-acetate, 1 mM EDTA) was heated for 2 minutes in a microwave to melt and evenly disperse the agarose. The solution was cooled at room temperature, and ethidium bromide (0.5 µg/ml) was added and poured into the apparatus. Each sample was mixed with 6× gel loading buffer (0.25% bromophenol blue, 0.25% xylene cyanol FF, 40% (w/v) sucrose in water). TAE buffer was used as the running buffer. Voltage (10 v/cm) was applied for 60-90 minutes.

According to the proper size for heavy and light chain cDNAs, the bands were excised from the gels under UV illumination, and excised gels were placed in 1 ml syringes fitted with 18-gauge needles. Gels were crushed to a 1.5 ml Eppendorf tube. The barrel of each syringe was washed with 200 µL of buffer-saturated phenol (pH 7.9.+/−.0.2). The mixture was thoroughly centrifuged and frozen at −70° C. for 10 minutes. The mixture was centrifuged for 5 minutes, and the top aqueous phase was transferred to a new tube. The aqueous phase was extracted again with phenol/chloroform (1:1). After centrifuging for 5 minutes, the top aqueous phase was transferred to a clean tube, and chloroform extraction was performed. Sodium acetate (10 volumes of 3 M) and 2.5 volumes of ice-cold ethanol were added to the top aqueous phase to precipitate DNA at −20° C. overnight.

Purified heavy and light chain cDNAs were ligated into plasmid pSTBlue-1 vector and transfected into NovaBlue competent cells (Stratagene). Colonies containing heavy and light chain DNAs were screened by blue and white colony selection and confirmed by PCR analysis. Heavy and light chain DNAs were isolated and sequenced using standard techniques.

PCR amplification and the assembly of single scFv gene was according to Davis et al. (1991) *Bio/Technology* 9:165-169. Plasmid pSTBlue-1 carrying VH and VL genes were combined with all four oligonucleotide primers in a single PCR synthesis. Following first PCR synthesis, one tenth of the first PCR product was removed and added to a second PCR reaction mixture containing only the primer a (VH sense primer) and primer d (VL Antisense primer). The product of the second PCR synthesis yielded single scFv gene. The single scFv gene was ligated to plasmid pT-Adv (Clontech, Palo Alto, Calif.). pT-Adv carrying scFv gene was used for DNA sequencing.

The complete functionalized scFv gene was assembled from the VH, VL and linker sequences to yield a scFv cDNA by PCR as follows:

DNA and Amino Acid Sequence of scFv(S)(GST) with Gly.Ser.Cys Linker [scFv(SC)]

Linker Sequence

```
DNA:
                                           SEQ ID NO: 4
5' GGCGGGGGTG GTAGCTGCGG CGGTGGATCG TGTGGCGGTG
GCAGT 3'.

Amino acid:
                                           SEQ ID NO: 5
GlyGlyGlyGlySerCytGlyGlyGlySerCytGlyGlyGlySer.
```

DNA and Amino Acid Sequence of scFv(GST)

GST-Tag

```
                                                        SEQ ID NO: 6
  1  ATGTCCCCTA TACTAGGTTA TTGGAAAATT AAGGGCCTTG TGCAACCCAC

51  TCGACTTCTT TTGGAATATC TTGAAGAAAA ATATGAAGAG CATTTGTATG

101  AGCGCGATGA AGGTGATAAA TGGCGAAACA AAAAGTTTGA ATTGGGTTTG

151  GAGTTTCCCA ATCTTCCTTA TTATATTGAT GGTGATGTTA AATTAACACA

201  GTCTATGGCC ATCATACGTT ATATAGCTGA CAAGCACAAC ATGTTGGGTG

251  GTTGTCCAAA AGAGCGTGCA GAGATTTCAA TGCTTGAAGG AGCGGTTTTG

301  GATATTAGAT ACGGTGTTTC GAGAATTGCA TATAGTAAAG ACTTTGAAAC

351  TCTCAAAGTT GATTTTCTTA GCAAGCTACC TGAAATGCTG AAAATGTTCG
```

-continued

```
401 AAGATCGTTT ATGTCATAAA ACATATTTAA ATGGTGATCA TGTAACCCAT
451 CCTGACTTCA TGTTGTATGA CGCTCTTGAT GTTGTTTTAT ACATGGACCC
501 AATGTGCCTG GATGCGTTCC CAAAATTAGT TTGTTTTAAA AAACGTATTG
551 AAGCTATCCC ACAAATTGAT AAGTACTTGA ATCCAGCAA GTATATAGCA
601 TGGCCTTTGC AGGGCTGGCA AGCCACGTTT GGTGGTGGCG ACCATCCTCC
651 AAAATCGGAT CTGGTTCCGC GTGGATCCCC AGGAATTCCC
``` scFv Heavy Chain (VH)

SEQ ID NO: 7
```
691  GAGGTCAAGC TGCAGGAGTC AGGAACTGAA GTGGTAAAGC CTGGGGCTTC
741  AGTGAAGTTG TCCTGCAAGG CTTCTGGCTA CATCTTCACA AGTTATGATA
791  TAGACTGGGT GAGGCAGACG CCTGAACAGG GACTTGAGTG GATTGGATGG
841  ATTTTTCCTG GAGAGGGGAG TACTGAATAC AATGAGAAGT TCAAGGGCAG
891  GGCCACACTG AGTGTAGACA AGTCCTCCAG CACAGCCTAT ATGGAGCTCA
941  CTAGGCTGAC ATCTGAGGAC TCTGCTGTCT ATTTCTGTGC TAGAGGGGAC
991  TACTATAGGC GCTACTTTGA CTTGTGGGGC CAAGGGACCA CGGTCACCGT
1041 CTCCTCA
```

Linker Sequence

DNA:
SEQ ID NO: 4
5' GGCGGGGGTG GTAGCTGCGG CGGTGGATCG TGTGGCGGTG
GCAGT 3'.

Amino acid:
SEQ ID NO: 5
GlyGlyGlyGlySerCytGlyGlyGlySerCytGlyGlyGlySer.

scFv Light Chain (VL)

SEQ ID NO: 8
```
1093 GAAAATGTGC TCACCCAGTC TCCAGCAATC ATGTCTGCAT CTCCAGGGGA
1143 GAGGGTCACC ATGACCTGCA GTGCCAGCTC AAGTATACGT TACATATATT
1193 GGTACCAACA GAAGCCTGGA TCCTCCCCCA GACTCCTGAT TTATGACACA
1243 TCCAACGTGG CTCCTGGAGT CCCTTTTCGC TTCAGTGGCA GTGGGTCTGG
1293 GACCTCTTAT TCTCTCACAA TCAACCGAAT GGAGGCTGAG GATGCTGCCA
1343 CTTATTACTG CCAGGAGTGG AGTGGTTATC CGTACACGTT CGGAGGGGGG
1393 ACCAAGCTGG AGCTGAAAGC G
```

DNA Sequence of scFv(SC) with GST Tag

SEQ ID NO: 9
```
  1 ATGTCCCCTA TACTACGTTA TTGGAAAATT AAGGGCCTTG TGCAACCCAC
 51 TCGACTTCTT TTGGAATATC TTGAAGAAAA ATATGAAGAG CATTTGTATG
101 AGCGCGATGA AGGTGATAAA TGGCGAAACA AAAAGTTTGA ATTGGGTTTG
151 GAGTTTCCCA ATCTTCCTTA TTATATTGAT GGTGATGTTA AATTAACACA
201 GTCTATGGCC ATCATACGTT ATATAGCTGA CAAGCACAAC ATGTTGGGTG
```

-continued

```
 251 GTTGTCCAAA AGAGCCTGCA GAGATTTCAA TGCTTGAAGG AGCGGTTTTG

301 GATATTAGAT ACGGTGTTTC GAGAATTGCA TATAGTAAAG ACTTTGAAAC

351 TCTCAAAGTT CATTTTCTTA GCAAGCTACC TGAAATGCTG AAAATGTTCG

401 AAGATCGTTT ATGTCATAAA ACATATTTAA ATGGTGATCA TGTAACCCAT

451 CCTGACTTCA TGTTGTATGA CGCTCTTGAT GTTGTTTTAT ACATGGACCC

501 AATGTGCCTG GATGCGTTCC CAAAATTAGT TTGTTTTAAA AAACGTATTG

551 AAGCTATCCC ACAAATTGAT AAGTACTTGA ATCCAGCAA GTATATAGCA

601 TGGCCTTTGC AGGGCTGGCA AGCCACGTTT GGTGGTGGCG ACCATCCTCC

651 AAAATCGGAT CTGGTTCCGC GTGGATCCCC AGGAATTCCC GAGGTCAAGC

701 TGCAGGAGTC AGGAACTGAA GTGGTAAAGC CTGGGGCTTC AGTGAAGTTG

751 TCCTGCAAGG CTTCTGGCTA CATCTTCACA AGTTATGATA TAGACTGGGT

801 GAGGCAGACG CCTGAACAGG GACTTGAGTG GATTGGATGG ATTTTTCCTG

851 GAGAGGGGAG TACTGAATAC AATGAGAAGT TCAAGGGCAG GGCCACACTG

901 AGTGTAGACA AGTCCTCCAG CACAGCCTAT ATGGAGCTCA CTAGGCTGAC

951 ATCTGAGGAC TCTGCTGTCT ATTTCTGTGC TAGAGGGGAC TACTATAGGC

1001 GCTACTTTGA CTTGTGGGGC CAAGGGACCA CGGTCACCGT CTCCTCAGGC

1051 GGGGGTGGTA GCTGCGGCGG TGGATCGTGT GGCGGTGGCA GTGAAAATGT

1101 GCTCACCCAG TCTCCAGCAA TCATGTCTGC ATCTCCAGGG GAGAGGGTCA

1151 CCATGACCTG CAGTGCCAGC TCAAGTATAC GTTACATATA TTGGTACCAA

1201 CAGAAGCCTG GATCCTCCCC CAGACTCCTG ATTTATGACA CATCCAACGT

1251 GGCTCCTGGA GTCCCTTTTC GCTTCAGTGG CAGTGGGTCT GGGACCTCTT

1301 ATTCTCTCAC AATCAACCGA ATGGAGGCTG AGGATGCTGC CACTTATTAC

1351 TGCCAGGAGT GGAGTGGTTA TCCGTACACG TTCGGAGGGG GACCAAGCT

1401 GGAGCTGAAA GCG
```

Translation of scFv(S)(GST) with Gly.Ser.Cys Linker DNA Sequence SEQ ID NO:10 and Amino Acid Sequence SEQ ID NO:11:

```
  1 atgtcccctatactaggttattggaaaattaagggccttgtgcaacccactcgacttctt
  1  M  S  P  I  L  G  Y  W  K  I  K  G  L  V  Q  P  T  R  L  L 61 ttggaatatcttgaagaaaaatatgaagagcatttgtatgagcgcgatgaaggtgataaa
 21  L  E  Y  L  E  E  K  Y  E  E  H  L  Y  E  R  D  E  G  D  K 121 tggcgaaacaaaaagtttgaattgggtttggagtttcccaatcttccttattatattgat
 41  W  R  N  K  K  F  E  L  G  L  E  F  P  N  L  P  Y  Y  I  D 181 ggtgatgttaaattaacacagtctatggccatcatacgttatatagctgacaagcacaac
 61  G  D  V  K  L  T  Q  S  M  A  I  I  R  Y  I  A  D  K  H  N 241 atgttgggtggttgtccaaaagagcgtgcagagatttcaatgcttgaaggagcggttttg
 81  M  L  G  G  C  P  K  E  R  A  E  I  S  M  L  E  G  A  V  L 301 gatattagatacggtgtttcgagaattgcatatagtaaagactttgaaactctcaaagtt
101  D  I  R  Y  G  V  S  R  I  A  Y  S  K  D  F  E  T  L  K  V 361 gattttcttagcaagctacctgaaatgctgaaaatgttcgaagatcgtttatgtcataaa
121  D  F  L  S  K  L  P  E  M  L  K  M  F  E  D  R  L  C  H  K 421 acatatttaaatggtgatcatgtaacccatcctgacttcatgttgtatgacgctcttgat
141  T  Y  L  N  G  D  H  V  T  H  P  D  F  M  L  Y  D  A  L  D
```

-continued

```
 481 gttgttttatacatggacccaatgtgcctggatgcgttcccaaaattagtttgttttaaa
 161  V  V  L  Y  M  D  P  M  C  L  D  A  F  P  K  L  V  C  F  K 541 aaacgtattgaagctatcccacaaattgataagtacttgaaatccagcaagtatatagca
 181  K  R  I  E  A  I  P  Q  I  D  K  Y  L  K  S  S  K  Y  I  A 601 tggcctttgcagggctggcaagccacgtttggtggtggcgaccatcctccaaaatcggat
 201  W  P  L  Q  G  W  Q  A  T  F  G  G  G  D  H  P  P  K  S  D 661 ctggttccgcgtggatccccaggaattcccgaggtcaagctgcaggagtcaggaactgaa
 221  L  V  P  R  G  S  P  G  I  P  E  V  K  L  Q  E  S  G  T  E 721 gtggtaaagcctggggcttcagtgaagttgtcctgcaaggcttctggctacatcttcaca
 241  V  V  K  P  G  A  S  V  K  L  S  C  K  A  S  G  Y  I  F  T 781 agttatgatatagactgggtgaggcagacgcctgaacagggacttgagtggattggatgg
 261  S  Y  D  I  D  W  V  R  Q  T  P  E  Q  G  L  E  W  I  G  W 841 attttcctggagaggggagtactgaatacaatgagaagttcaagggcagggccacactg
 281  I  F  P  G  E  G  S  T  E  Y  N  E  K  F  K  G  R  A  T  L 901 agtgtagacaagtcctccagcacagcctatatggagctcactaggctgacatctgaggac
 301  S  V  D  K  S  S  S  T  A  Y  M  E  L  T  R  L  T  S  E  D 961 tctgctgtctatttctgtgctagaggggactactataggcgctactttgacttgtggggc
 321  S  A  V  Y  F  C  A  R  G  D  Y  Y  R  R  Y  F  D  L  W  G 1021 caagggaccacggtcaccgtctcctcaggcggggtggtagctgcggcggtggatcgtgt
 341  Q  G  T  T  V  T  V  S  S  G  G  G  G  S  C  G  G  G  S  C 1081 ggcggtggcagtgaaaatgtgctcacccagtctccagcaatcatgtctgcatctccaggg
 361  G  G  G  S  E  N  V  L  T  Q  S  P  A  I  M  S  A  S  P  G 1141 gagagggtcaccatgacctgcagtgccagctcaagtatacgttacatatattggtaccaa
 381  E  R  V  T  M  T  C  S  A  S  S  S  I  R  Y  I  Y  W  Y  Q 1201 cagaagcctggatcctcccccagactcctgatttatgacacatccaacgtggctcctgga
 401  Q  K  P  G  S  S  P  R  L  L  I  Y  D  T  S  N  V  A  P  G 1261 gtcccttttcgcttcagtggcagtgggtctgggacctcttattctctcacaatcaaccga
 421  V  P  F  R  F  S  G  S  G  S  G  T  S  Y  S  L  T  I  N  R 1321 atggaggctgaggatgctgccacttattactgccaggagtggagtggttatccgtacacg
 441  M  E  A  E  D  A  A  T  Y  Y  C  Q  E  W  S  G  Y  P  Y  T 1381 ttcggagggggaccaagctggagctgaaagcg
 461  F  G  G  G  T  K  L  E  L  K  A
```

Translated Protein Sequence:

```
                                                         SEQ ID NO: 11
  1 MSPILGYWKI KGLVQPTRLL LEYLEEKYEE HLYERDEGDK WRNKKFELGL EFPNLPYYID

61 GDVKLTQSMA IIRYIADKHN MLGGCPKERA EISMLEGAVL DIRYGVSRIA YSKDFETLKV

121 DFLSKLPEML KMFEDRLCHK TYLNGDHVTH PDFMLYDALD VVLYMDPMCL DAFPKLVCFK

181 KRIEAIDQID KYLKSSKYIA WPLQGWQATF GGGDHPPKSD LVPRGSPGIP EVKLQESGTE

241 VVKPGASVKL SCKASGYIFT SYDIDWVRQT PEQGLEWIGW IFPGEGSTEY NEKFKGRATL

301 SVDKSSSTAY MELTRLTSED SAVYFCARGD YYRRYFDLWG QGTTVTVSSG GGGSCGGGSC
                                                                     linker
361 GGGSENVLTQ SPAIMSASPG ERVTMTCSAS SSIRYIYWYQ QKPGSSPRLL IYDTSNVAPG

421 VPFRFSGSGS GTSYSLTINR MEAEDAATYY CQEWSGYPYT FGGGTKLELK A
```

Analysis of Protein Sequence:

Length in amino acids: 477

Molecular weight in kD: 53.52

Iso-electric point (IP): 5.87

Molar absorption coefficient (in L/mol/cm); all cysteine residues as disulfide bonds: 1.02E+05

Molar absorption coefficient (in L/mol/cm); 50 percent of cysteine residues as disulfide bonds: 1.02E+05

Molar absorption coefficient (in L/mol/cm); no disulfide bonds: 1.01E+05 scFv(S) heavy chain N-terminus (primer 15)
SEQ ID NO: 12
5' GGA TCC CCA GGA ATT CCC GAG GTC AAG CTG CAG GAG TCA GGA '
              EcoRI 1. Primer Design
Linker with Gly.Ser.Cys Amino acid sequence:
SEQ ID NO: 5
GlyGlyGlyGlySerCytGlyGlyGlySerCytGlyGlyGlySer DNA sequence:
SEQ ID NO: 4
5'-GGCGGGGGTG GTAGCTGCGG CGGTGGATCG TGTGGCGGTG GCAGT-3'

Design for Primers
1. Forward Primer for scFv(S) Heavy Chain for PCR Amplification 2. Reverse Primer for scFv(S) Heavy Chain for PCR Amplification
scFv(S) Heavy Chain C-Terminus Plus Linker 1

SEQ ID NO: 13
Amino acid seq: GTTVTVSS
              heavy chin C-terminus

SEQ ID NO: 14
GGGGSCGGGSCGGGS
   linker

SEQ ID NO: 15
    GGGACCACGG TCACCGTCTC CTCAGGCGGG GGTGGTAGCT GCGGCGGTGG
1

51   ATCGTGTGGC GGTGGCAGT

SEQ ID NO: 16
GGGACCACGGTCACCGTCTCCTCAGGCGGGGGTGGTAGCTGCGGCGGTGGATCGTGTGGC
1
1    G T T V T V S S G G G G S C G G G S C G
61   GGTGGCAGT
21   G G S

Reverse Primer for scFv(S) Heavy Chain for PCR Amplification (Primer 18):

SEQ ID NO: 17
5'ACC GCC ACA CGA TCC ACC GCC GCA GCT ACC ACC CCC GCC TGA GGA GAC GGT GAC CGT GGT CCC 3'

3. Forward Primer for scFv(S) Light Chain PCR Amplification
Linker Plus scFv(S) Light N-Terminus SEQ ID NO:18

Amino acid seq: G GSC GGG SCG GGS        ENV LTO SP
          Linker                  light chain N-terminus 1 GGTGGTAGCTGCGGCGGTGGATCGTGTGGCGGTGGCAGTGAAAATGTGCTCACCCAGTCT  SEQ ID NO: 19
1 G G S C G G G S C G G G S E N V L T Q S  SEQ ID NO: 20

61 CCA
21 P

Forward Primer for scFv(S) Light Chain for PCR Amplification (Primer 19):

SEQ ID NO: 21
5' GGT GGT AGC TGC GGC GGT GGA TCG TGT GGC

GGT GGC AGT GAA AAT GTG CTC ACC CAG TCT CCA 3'

4. Reverse Primer for scFv(S) Light Chain for PCR Amplification (Primer 17)

Sense DNA seq:
SEQ ID NO: 22
5' GAACGCCAGCACATGGACAGCTGACTCGAGCGGCCGGTG 3'

Antisense DNA seq:
SEQ ID NO: 23
5' CACCGGCCG<u>CTCGAG</u>TCAGCTGTCCATGTGCTGGCGTTC 3'
              XhoI Primers were ordered from Integrated DNA Technologies (Coralville, Iowa). PCR amplification of heavy chain ($V_H$) and light chain ($V_L$) of scFv(SC). Heavy chain and light chain of scFv(SC) were amplified by polymerase chain reaction (PCR).
Conditions for PCR were:

| 1) PCR of heavy chain | |
|---|---|
| 10x pfu DNA polymerase buffer | 5 µl |
| dNTP mix | 1 µl |
| Forward primer (Primer 15) | 1 µl |
| Reverse primer (Primer 18) | 1 µl |
| pGEX4T-scFv(SE) | 0.2 µl |
| pfu DNA polymerase | 0.25 µl |
| Taq DNA polymerase (10x diluted) | 0.2 µl |
| Water | 41.35 µl |
| Total | 50 µl |
| 2) PCR of light chain | |
| 10x pfu DNA polymerase buffer | 5 µl |
| dNTP mix | 1 µl |
| Forward primer (Primer 19) | 1 µl |
| Reverse primer (Primer 17) | 1 µl |
| pGEX4T-scFv(SE) | 0.2 µl |
| pfu DNA polymerase | 0.25 µl |
| Taq DNA polymerase (10x diluted) | 0.2 µl |
| Total | 50 µl |

PCR Cycle

| 94° C. | 3 minutes | 1 cycle |
|---|---|---|
| 94° C. | 30 seconds | 30 cycles |
| 64° C. | 30 seconds | |
| 72° C. | 2 minutes | |
| 72° C. | 10 minutes | 1 cycle |

Heavy chain and light chain DNAs of scFv(SC) was analyzed by agarose gel electrophoresis (0.9%). DNA bands were excised, frozen, thawed and centrifuged. scFv(SC) DNA was amplified by extending heavy chain and light chain DNAs by PCR.
Conditions for PCR were:

| 10x pfu DNA polymerase buffer | 10 µl | 94° C. | 3 minutes | 1 cycle |
|---|---|---|---|---|
| dNTP mix | 2 µl | 94° C. | 30 seconds | 30 cycles |
| | | 64° C. | 30 seconds | |
| Forward primer (Primer 15) | 2 µl | 72° C. | 2 minutes | |
| | | 72° C. | 10 minutes | 1 cucle |
| Reverse primer (Primer 17) | 2 µl | | | |
| Heavy chain DNA | 5 µl | | | |
| Light chain DNA | 5 µl | | | |
| pfu DNA polymerase | 0.5 µl | | | |
| Taq DNA polymerase (10x diluted) | 0.1 µl | | | |
| Water | 74.4 µl | | | |
| Total | 100 µl | | | |

The amplified scFv(SC) DNA was analyzed by agarose gel electrophoresis (0.9%). DNA bands were excised, purified by QIAquick Gel Extraction Kit (QIAGEN) and solubilized in 30 µl of TE buffer.

| 1) Digestion with EcoRI | | Digestion was 2 hr at 37° C. |
|---|---|---|
| 10x NE4 buffer | 5 µl | Enzyme was heat inactivated at |
| scFv(SC) | 25 µl | 65° C. 15 minutes. |
| EcoRI HF (20 Units) | 1 µl | DBNA was precipitated by ethanol |
| Water | 19 µl | precipitation. |
| | 50 µl | |
| 2) Digestion with XhoI | | Digestion was 1 hr 24 min at 37° C. |
| 10x React 2 buffer | 5 µl | Solution was heated at 65° C. 20 min. |
| scFv(SC) | 44 µl | DBNA was precipitated by ethanol |
| XhoI (10 Units) | 1 µl | precipitation. |
| | 50 µl | DNA was purified by agarose gel electrophoresis (0.9%) and purified. Concentration was 26.4 ng/µl in 30 µl of TE buffer. |

Ligation of scFv(SC) to pGEX-4T2 [pGEX4T-scFv(SC)]. scFv(SC) was ligated to pGEXT-4T2. The ligation reaction was as follows:

| Digestion with EcoRI | |
|---|---|
| 10x T4 DNA ligase buffer | 2 µl |
| pGEX-4T2 digested with EcoRI and XhoI (200 ng) | 1.13 µl |
| scFv(SC) digested with EcoRI and XhoI (100 ng) | 25 µl |
| T4 DNA ligase | 1.5 µl |
| Water | 11.5 µl |
| | 20 µl |

Ligation was 16 hours 50 minutes at 15° C. After ligation, E. coli BL21 (DE3) cells were transformed with pGEX4T-scFv(SC) and plated on LB/ampicillin plate. Cells were grown 37° C. for 20 hours. Screening of colonies for carrying plasmid pGEX4T-scFv(SC). Seven colonies were screened for carrying plasmid pGEX4T-scFv(SC) by PCR.

| 5x Green GoTaq DNA polymerase buffer | 30 µl | 94° C. | 2 min | 1 cycle |
|---|---|---|---|---|
| | | 94° C. | 30 sec | |
| 25 mM MgCl$_2$ | 15 µl | 64° C. | 30 sec | 30 cycles |
| dNTP mix | 3 µl | 72° C. | 45 sec | |
| Forward primer (Primer 15) | 3 µl | 72° C. | 10 min | 1 cycle |
| Reverse primer (Primer 18) | 3 µl | | | |

| | |
|---|---|
| Heavy chain DNA | 5 μl |
| Colony DNA | 35 μl |
| Taq DNA polymerase | 1.5 μl |
| Water | 59.5 μl |
| Total | 150 μl |

Reaction volume was 20 μl per colony.

Cells were picked from colony 1, grown in 100 ml of LB/ampicillin media and plasmid was purified using plasmid purification kit (Plasmid Midi Kit, Qiagen). scFv(SC) DNA sequence was performed by Purdue University. The sequenced DNA was analyzed by Alignment algorithm (NCBI) and showed no mutation.

Sequence scFv(SC) DNA with primers 15 and 17

```
>L_132420_Primer15_025.ab1 1464 21 860 ABI
                                         SEQ ID NO: 24
AAAAAACAATGCAAAGTGGTAAAAGCCTGGGGCTTCAGTGAAGTTGTCCT
GCAAGGCTTCTGGCTACATCTTCACAAGTTATGATATAGACTGGGTGAGG
CAGACGCCTGAACAGGGACTTGAGTGGATTGGATGGATTTTTCCTGGAGA
GGGGAGTACTGAATACAATGAGAAGTTCAAGGGCAGGGCCACACTGAGTG
TAGACAAGTCCTCCAGCACAGCCTATATGGAGCTCACTAGGCTGACATCT
GAGGACTCTGCTGTCTATTTCTGTGCTAGAGGGGACTACTACAGGCGCTA
CTTTGACTTGTGGGGCCAAGGGACCACGGTCACCGTCTCCTCAGGCGGGG
GTGGTAGCTGCGGCGGTGGATCGTGTGGCGGTGGCAGTGAAAATGTGCTC
ACCCAGTCTCCACCAATCATGTCTGCATCTCCAGGGGAGAGGGTCACCAT
GACCTGCAGTGCCAGCTCAAGTATACGTTACATATATTGGTACCAACAGA
AGCCTGGATCCTCCCCAGACTCCTGATTTATGACACATCCAACGTGGCT
CCTGGAGTCCCTTTTCGCTTCAGTGGCAGTGGGTCTGGGACCTCTTATTC
TCTCACAATCAACCGAATGGAGGCTGAGGATGCTGCCACTTATTACTGCC
AGGAGTGGAGTGGTTATCCGTACACGTTCGGAGGGGGGACCAAGCTGGAG
CTGAAAGCGAAAGAAACTGCTGCTGCTAAATTCGAACGCCAGCACATGGA
CAGCTGACTCGAGCGGCCGCATCGTGACTGACTGACGATCTGCCTCGCGC
GTTTCGGTGATGACGGTGAAAACCTCTGACACATGCAGCTCCCGGAGACG
GTCACAGCTTGTCTGTAAGCGGATGCCGGGAGCAGACAAGCCCGTCAGGG
CGCGTCAGCGGGTGTTGGCGGGTGTCCGGGCCCCGCCATGACCCAGTCAC
GTAGCGATAGCGGAGTGTATAATTCTTGAAGACGAAAGGGCCTCGTGAAT
CGCCTATTTTTATAGGGTAATGTCATGATAATAATGGTTTCTTAAACGTC
AAGGGGGCACTTTTTCGGGAAATGTGCGCCGAAACCCCTAATTTGTTTTA
TTTTTCAAAATCCATTTCAATTAAGTTTCCCCCTCATGGAAACAATAACC
CCTGGAAAAAAGGCTTTCATTAAATATTGAAAAAAAGGAAAAAAGTTAAA
AATTATTTCAAAATTTTCCCTGTGTTCCCCCCTTTATTTTCCCTTTTTT
TTGCGGGCCATTTTTTGCCCTTTTCCCTGGTTTTTTTTGCCCCCCCCCC
CAAAAAAACCCCCCTGGGGTGAAAAAAAAATAAAAAAAAAAAATGTCTTT
AAAAAAAAATTTCCAATTTTTGTGGGGGGGGGCCCCCCCAAAAGAGTTG
GGGGGGTTTTTTAAACCACTTCTCCCAAAACAACATTGGGTGGAGATATT
TCTTCTTCACAAAA >L_132420_Primer17_026.ab1 1492 22 854 ABI
                                         SEQ ID NO: 25
GGTGGGTAAATTTAGCAGCAGCAGTTTCTTTCGCTTTCAGCTCCAGCTTG
GTCCCCCCTCCGAACGTGTCCGGATAACCACTCCACTCCTGGCAGTAATA
AGTGGCAGCATCCTCAGCCTCCATTCGGTTGATTGTGAGAGAATAAGAGG
TCCCAGACCCACTGCCACTGAAGCGAAAAGGGACTCCAGGAGCCACGTTG
GATGTGTCATAAATCAGGAGTCTGGGGGAGGATCCAGGCTTCTGTTGGTA
CCAATATATGTAACGTATACTTGAGCTGGCACTGCAGGTCATGGTGACCC
TCTCCCCTGGAGATGCAGACATGATTGCTGGAGACTGGGTGAGCACATTT
TCACTGCCACCGCCACACGATCCACCGCCGCAGCTACCACCCCCGCCTGA
GGAGACGGTGACCGTGGTCCCTTGGCCCCACAAGTCAAAGTAGCGCCTGT
AGTAGTCCCCTCTAGCACAGAAATAGACAGCAGAGTCCTCAGATGTCAGC
CTAGTGAGCTCCATATAGGCTGTGCTGGAGGACTTGTCTACACTCAGTGT
GGCCCTGCCCTTGAACTTCTCATTGTATTCAGTACTCCCCTCTCCAGGAA
AAATCCATCCAATCCACTCAAGTCCCTGTTCAGGCGTCTGCCTCACCCAG
TCTATATCATAACTTGTGAAGATGTAGCCAGAAGCCTTGCAGGACAACTT
CACTGAAGCCCCAGGCTTTACCACTTCAGTTCCTGACTCCTGCAGCTTGA
CCTCGGGAATTCCAGAAAGGGCCTGCTTGAACTTCTCCTTTGCTTCTTCC
ATATCTTTCTCATGGGCGGATCCACGCGGAACCAGATCCGATTTTGGAGG
ATGGTCGCCACCACCAAACGTGGCTTGCCAGCCCTGGCAAGGCCATGCTA
TATACTTGCTGGATTTCAAGTACTTATCAATTTGTGGGAATAGCTTCCTT
ACGTTTTTTAAAACAAACTAATTTTGGGAACGCATCCAGGCCCATTTGG
TCCATGTATTAAAACACCATCAAAAACCTCCTACAACATGAAATTCCGGA
AGGGGTTTACATAATCCCCCATTTTAAATATTGTTTTTATGACATAAAAC
CAATCTTTCCAAACTTTTTTTCACATTTTCCAGGTAACCTTGGTAAAAAA
AAAACCACTTTTGAAAAGTTTTTCAAAATTCTTTTTATTAAAATGCAAAT
TTTCCCGAAAAAAACCCCTTATTTCTAAAAATTCCCAAAAACCCGCTCCC
CTTTTCCAAGCCCTTTGAAAAATTTCTTTGCCCCCCCCCTCTTTTTTGGGG
AACAAAACCCCCCCCCACAAACTTGGGTTGGGGGTGGTTTTTGTGTCCAC
GCCCAAATATAAAAAACAGTATAAATTAAGATGGGGCCCCCACATATAA
AAAACTGGGGGGGTTTTTTTATATAATTTTTAAAACACAACATCCCCC
CCCCCCCCCCACATCCCACACAAAATAAAATATATAATAAAA
```

Alignment of scFv(SC) with Sequenced DNA
Expression of scFv(SC)

BL21(DE3) cells carrying plasmid pGEX4T-scFv(SC) was inoculated in 10 ml of LB/carbenicillin (100 μg/ml). Cells were grown for 6 hr and centrifuged at 6,000 rpm (3,700×g) for 6 minutes. Supernatant was discarded and pellet was resuspended in fresh 2 ml of LB/ampicillin (100 μg/ml) and transferred to two 100 ml LB/amp media in 250 ml-Erlenmyer flask. Cells were grown 3 hours at 37° C. at 250 rpm. Temperature was lowered to 25° C. and IPTG was added (0.15 mM final concentration). Cells were grown additionally 15 hours, harvested and resuspended in 20 ml of 20 mM Tris-HCl, pH 8.0 buffer. Proteins were extracted by French Pressure (3 passages at 20,000 psi). Expression of scFv(SC) was analyzed by SDS-PAGE followed by Ponceau S staining and western blot.

scFv(SC) was expressed both as soluble protein and as insoluble inclusion bodies.

1D Western blot analysis of scFvSC. Reactivity of scFv (SC) toward recombinant ENOX2 was analyzed by 1 dimensional western blot. Recombinant ENOX2 was separated by SDS-PAGE and transferred to nitrocellulose membranes. Nitrocellulose membranes were incubated with scFv(SC) for 17 hours and alkaline phosphatase linked S-protein for 2 hours. Detection was with Western Blue (Promega). scFv A major factor, however, in determining the efficacy of the scFv is its propensity to aggregate. After only ten days of storage at either −70° C. or 4° C., the binding of the purified scFv to recombinant ENOX2 protein was reduced by more than 90%. After much study, this loss of efficacy was traced solely to protein aggregation. Aggregated antibodies do not combine specifically with ENOX2 proteins during western blotting. Aggregation of the functionalized scFv antibody as determined from light scattering measurements is achieved by storage in 50% glycerol and stored at −70° C., essential ingredients in the overall protocol to achieve the desired level of sensitivity and specificity. Activity is lost rapidly by storage in the absence of glycerol.

TABLE 4

Detection of ENOX2 transcript variants and reference proteins comparing functionalized scFv recombinant antibodies stored in the presence or absence of 50% glycerol.

| | scFv stored in the absence of 50% glycerol | | | | scFv stored in the presence of 50% glycerol | | | |
|---|---|---|---|---|---|---|---|---|
| Cancer | Ref. pH 4.1 | Ref pH 6.8 | Ref 3 | Spot | Ref. pH 4.1 | Ref pH 6.8 | Ref 3 | Spot |
| Prostate | + | + | − | +/− | + | + | + | +/− |
| Colorectal | + | + | − | +/− | ++ | ++ | + | ++ |
| Breast, Bladder | + | + | − | + | ++ | ++ | + | + |
| NSC Lung | + | + | − | + | ++ | ++ | + | + |
| Testicular | + | + | − | +/− | ++ | ++ | + | + |
| Blood Cell | + | + | − | +/− | ++ | ++ | + | + |
| Overall | + | + | − | +/− | ++ | ++ | + | + |

(SC) reacted toward recombinant ENOX2. For comparison, scFv(S) was included in the western blot analysis.

Figure 12:
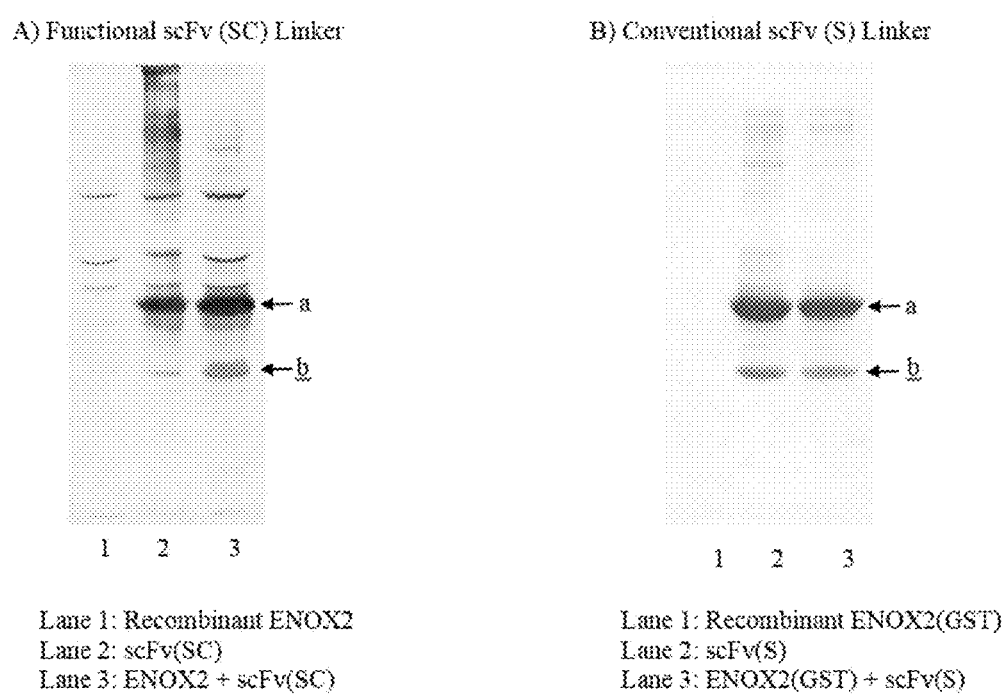
FIG. 12 shows Western blots of mixing experiments to demonstrate efficacy of ScFV with —CXXC—XX—C linker (FIG. 12A) compared to the conventional XXXXXXX linker (FIG. 12B). Under non-reducing conditions for both (to preserve S—S bonds), the ScFV recombinant antibody with the functional cysteine linker when incubated with recombinant ENOX2 showed reduced levels of 53 kDa ScFV (a) and a 46 kDa truncated ScFV from a downstream initiation site (b) predominantly by disulfide bond formation between the full length ScFV and the 72 kDa full length ENOX2 in a ratio of one ENOX2 molecule plus two ScFV molecules (one to each of the two protein disulfide isomerase binding sites of ENOX2) for a combined molecular weight of about 176 kDa.

FIG. 12 shows Western blots of mixing studies to demonstrate efficacy of ScFV with —CXXC—XX—C linker (FIG. 12A) compared to the conventional XXXXXXX linker (FIG. 12B). Under non-reducing conditions for both (to preserve S—S bonds), the ScFV recombinant antibody with the functional cysteine linker when incubated with recombinant ENOX2 showed reduced levels of 53 kDa ScFV (a) and a 46 kDa truncated ScFV from a downstream initiation site (b) predominantly by disulfide bond formation between the full length ScFV and the 72 kDa full length ENOX2 in a ratio of one ENOX2 molecule plus two ScFV molecules (one to each of the two protein disulfide isomerase binding sites of ENOX2) for a combined molecular weight of about 176 kDa. In FIG. 12B, with the conventional linker lacking cysteines, no evidence of cross-linking under identical reaction conditions was observed.

2D Western blot analysis of scFvSC. Reactivity of scFv (SC) toward recombinant ENOX2 and transcript variant of serum of prostate cancer patient was analyzed by 2 dimensional western blot. Normal serum spiked with 6 μg of recombinant and serum from prostate cancer patient were separated first by isoelectric focusing and then SDS-PAGE and then transferred to nitrocellulose membranes. Nitrocellulose membranes were incubated with scFv(SC) for 17 hours and alkaline phosphatase linked S-protein for 2 hours. Detection was with Western Blue (Promega).

Method 5—Enhancement of the Physical Stability of Concentrated Antibody Solutions An important embodiment of the present invention is to enhance the physical stability of concentrated solutions, while maintaining chemical stability and biological potency. The invention provides scFv antibodies which are at least 99% identical to SEQ ID NO:11 and have a kDa for ENOX2 protein of $7 \times 10^{-7}$ M and a purity of at least 95%.

With storage in the presence of 50% glycerol (right), all three reference proteins were approximately two times stronger than in the absence of glycerol (left). Transcript variants (spots) were clearer with storage in 50% glycerol (right) than in its absence (left)

Figure 13:
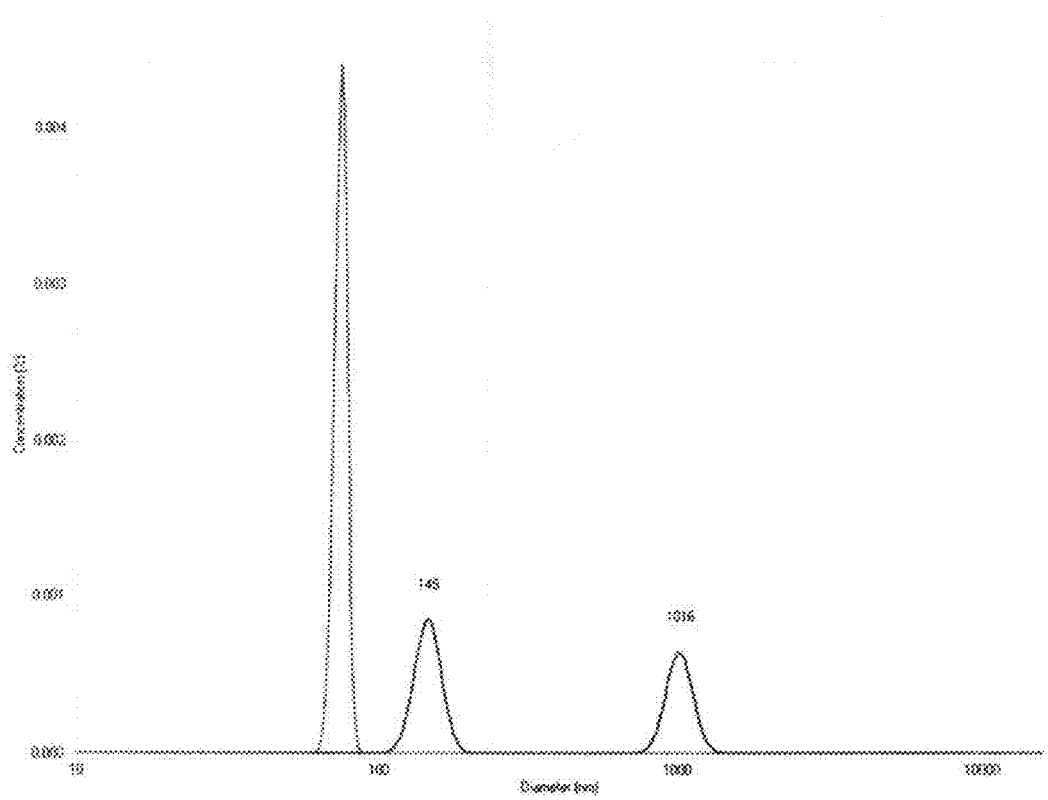
FIG. 13 is particle distribution as concentration (%) of antibody based on size (nm) determined by light scattering (Agilent 7080 Particle Size Spectrophotometer) showing predominately the major contribution of unaggregated antibody when stored in 50% glycerol at −70° C.

FIG. 13 is particle distribution as concentration (%) of antibody based on size (nm) determined by light scattering (Agilent 7080 Particle Size Spectrophotometer) showing predominately the major contribution of unaggregated antibody when stored in 50% glycerol at −70° C.

These three elements, addition of NADH during antibody binding, modification of the scFv linker peptide to resemble the ENOX2 protein disulfide-thiol interchange functional motif and the use of 50% glycerol to prevent scFv aggregation combine to provide an unprecedented sensitivity of the ONCOblot test to permit detection of cancers more than 10 years in advance of clinical symptoms.

Method 6—Determination of the Sensitivity and Limit of Detection of the Functionalized Antibody in the Presence of NADH.

The incidence of confirmed false positives and confirmed false negatives is low, less than 1% each (D. J. Morre and D. S. Gilmartin. 2015 *ONCOblot Reports* 1 (1):1-2). For several cancers, two or more ENOX2 transcript variants must be present within the ONCOblot Tissue of Origin Cancer Test to permit the correct identification of the tissue of origin. These include bladder, colorectal, gastric, mesothelioma, ovarian, renal cell and uterine cancer. If one or more ENOX2 transcript variants are absent or below the limit of detection, the tissue of origin of the cancer may be misidentified. Of the most recent ONCOblots analyzed under the current protocol, the rate of misidentification is 2.8%. Thus, the overall accuracy of the test with clinically diagnosed cancers is at least 95%.

When proteins are separated by two-dimensional (2-D) gel electrophoresis and detected by immunoblot, visualized proteins appear as small spherical or oval immunoreactive regions termed "spots." The average diameter of the spot produced by an ENOX2 protein is proportional to the amount of ENOX2 protein present. To determine the limit of ENOX2 detection by ONCOblot, a standard cure of spot diameter was generated. To this end, a functional 46 kDa form of human ENOX2 was first produced in E. coli and purified to near homogeneity. Various amounts of this recombinant ENOX2 protein were then assayed by ONCOblot. The log of the resulting spot diameter was then plotted against the log of the amount of ENOX2 protein assayed (FIG. 11) and a strong linear correlation ($r^2=0.95$) was found among the values. The practical lower limit of detection of an ENOX2 protein assayed by ONCOblot is a spot on the order of 0.25 mm, which by comparison to FIG. 11 correlated to the detection of 120 femtomoles ($1.2 \times 10^{11}$ molecules) of ENOX2 per assay. This value is approximately equivalent to a lower limit of 100 femtomoles of ENOX2 per assay.

Figure 11:
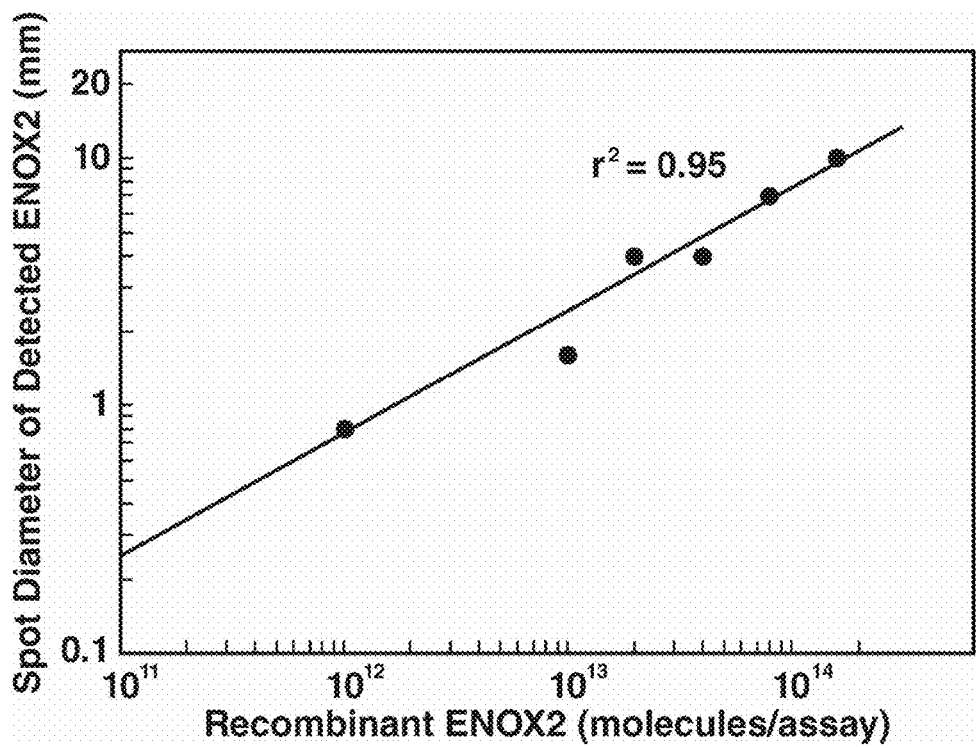
FIG. 11 illustrates the log-log relationship between spot diameter and amount of ENOX2 protein loaded on the 2-D gel. Varying amounts of recombinant ENOX2 were analyzed by immunoblot. The log of the diameter of the detected ENOX2 spot was then plotted as a function of the log of the amount of ENOX2 loaded.

FIG. 11 illustrates the log-log relationship between spot diameter and amount of ENOX2 protein loaded on the 2-D gel. Varying amounts of recombinant ENOX2 were analyzed by immunoblot. The log of the diameter of the detected ENOX2 spot was then plotted as a function of the log of the amount of ENOX2 loaded.

FIG. 12 shows Western blots of mixing experiments to demonstrate efficacy of ScFV with —CXXC—XX—C linker (FIG. 12A) compared to the conventional XXXXXXX linker (FIG. 12B). Under non-reducing conditions for both (to preserve S—S bonds), the ScFV recombinant antibody with the functional cysteine linker when incubated with recombinant ENOX2 showed reduced levels of 53 kDa ScFV (a) and a 46 kDa truncated ScFV from a downstream initiation site (b) predominantly by disulfide bond formation between the full length ScFV and the 72 kDa full length ENOX2 in a ratio of one ENOX2 molecule plus two ScFV molecules (one to each of the two protein disulfide isomerase binding sites of ENOX2) for a combined molecular weight of about 176 kDa. In FIG. 12B, with the conventional linker lacking cysteines, no evidence of cross-linking under identical reaction conditions was observed.

FIG. 13 is particle distribution as concentration (%) of antibody based on size (nm) determined by light scattering (Agilent 7080 Particle Size Spectrophotometer) showing predominately the major contribution of unaggregated antibody when stored in 50% glycerol at −70° C.

Figure 14:
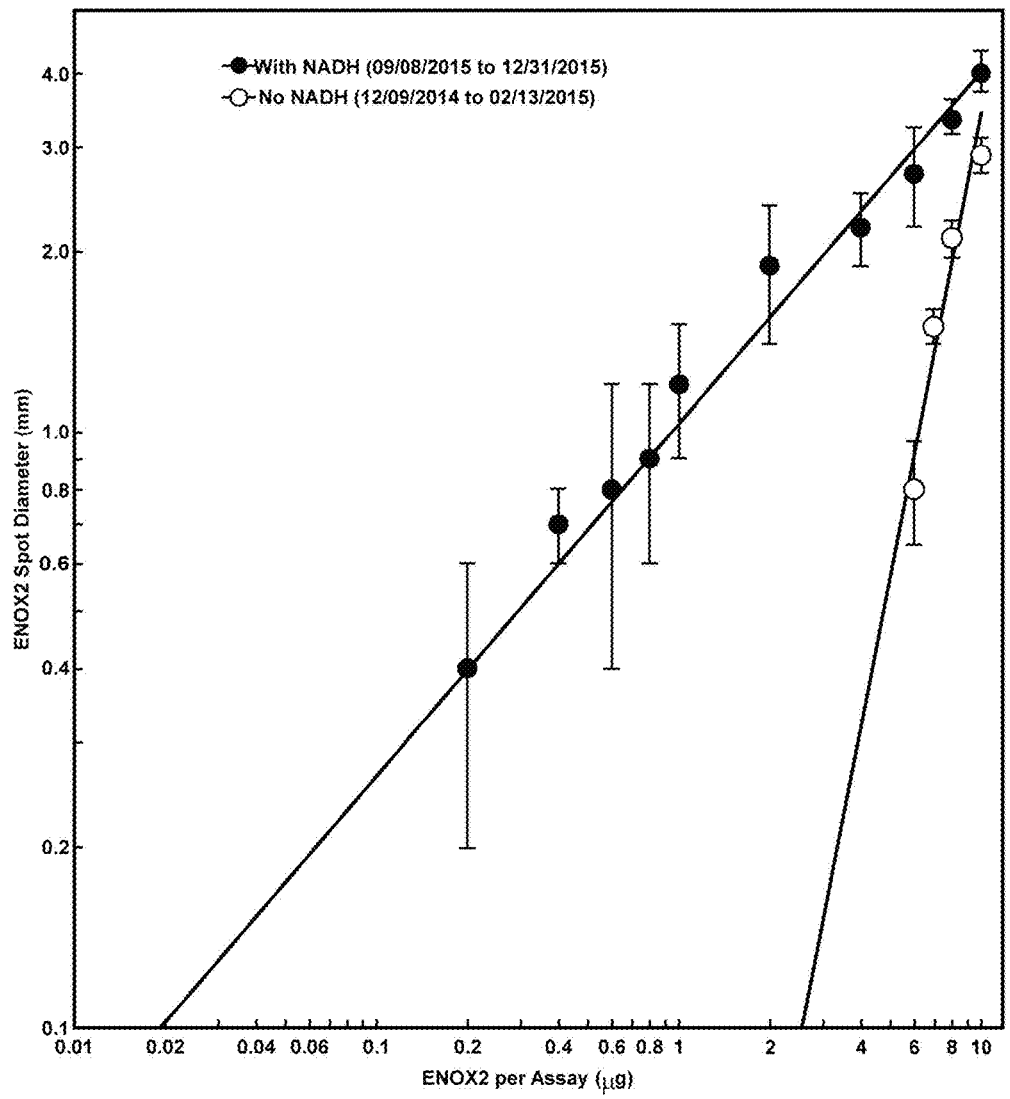
FIG. 14 is a comparison of the NADH-targeted two-dimensional western blot analysis described herein compared with a conventional two-dimensional western blot analysis as described by Hostetler et al. 2009 (*Clin. Proteomics* 5: 46-51) validating a 10-fold increase in sensitivity of ENOX2 transcript variant detection.

ENOX2 proteins within sera of 25 Stage 0 and Stage I cancer patients were detected by ONCOblot (Morre, D. J and Taggart, D. J. 2015. *ONCOblot Reports* 1(4):1-2). The average concentration of ENOX2 within these sera samples was approximately 990 femtomoles ($6 \times 10^{11}$ molecules) per 150 µL assay by comparison to the standard curve of FIG. 11. By definition, Stage 0 and Stage I cancers are typically less than 20 mm in diameter (Cancer Facts and Figures. 2014. *Amer Can Soc* 2-3). However, as the average size of Stage 0 or Stage I cancer is more likely to be 5 to 10 mm in diameter, the lower limit of detection of ENOX2 would be predicted to be produced by a 0.8 mm to 1.6 mm diameter tumor (1.2 mm average). A comparison of the lower limit of detection of recombinant ENOX2 between the previous version of the ONCOblot test (Hostetler et al., 2009. *Clinical Proteomics* 5: 46-51) and the current version of the test with NADH and functionalized scFv antibody is provided in FIG. 14. With NADH and the functionalized scFv antibody the lower limit of detection of recombinant ENOX2 in the protocol is about 5 µg. With the functionalized test using NADH and the modified linker the limit of detection is approximately 10-fold lower (curve on the right).

If the tumor cells are treated as spheres, then the number of cells in a solid tumor can be calculated by using equation 1, where $V_{tumor}$ is the volume of the tumor, $V_{cell}$ is the average volume of a cancer cell, D is the tumor diameter and d is the average diameter of a cancer cell estimated to be 10 um, then a 1.2 mm diameter cancer is calculated to contain approximately 2 million cells.

$$\text{\# tumor cells} = \frac{V_{tumor}}{V_{cell}} = \frac{\frac{4}{3}\pi\left(\frac{D}{2}\right)^3}{\frac{4}{3}\pi\left(\frac{d}{2}\right)^3} = \frac{\left(\frac{D}{2}\right)^3}{\left(\frac{d}{2}\right)^3} = \left(\frac{\frac{D}{2}}{\frac{d}{2}}\right)^3 = \left(\frac{D}{d}\right)^3 \quad \text{Equation 1}$$

Method 7—How Early Might the Functionalized Test with NADH and Modified Linker Detect Cancer in Advance of Clinical Symptoms.

Evidence summarized herein has determined that the capability of the test in its present configuration is to detect cancer between 10 and 20 years in advance of clinical symptoms consistent with the 10-fold increased sensitivity provided.

In order to estimate how far in advance if clinical symptoms it would be possible to detect cancer presence by the current functionalized version of the test, a study was designed to determine, by comparison to NCI Seer Cancer Statistics Review (Howlander, N. et al. SEER Cancer Statistics Review, 1875-2912, National Cancer Institute, Bethesda, Md.) estimation of how closely the current test results correlated with overall risk of being diagnosed with cancer comparing six age groups consisting of equal numbers of male and female participants. Actual diagnoses were compared to those predicted by the Seer Cancer Statistics Review of predicted risk of being diagnosed with cancer with increasing age.

A total of 300 healthy volunteers without clinical evidence of cancer, 25 males and 25 females in each of six age groups, were analyzed for cancer presence by the current 2-D gel-western blot test with NADH and functionalized linker. Sera were collected by venipuncture and analyzed using IRB approved protocols and informed consent. Findings summarized in Table 5 reveal a relatively high incidence of early cancer detection with the normal healthy population consistent with cancer detection 10 to 20 years in advance of clinical symptoms (see also FIG. 5).

TABLE 5

Incidence of early cancer detected by the current 2-D gel-Western blot test with NADH and functionalized linker in a normal population of healthy male and female volunteers.

| | Tests positive for cancer (%) | | |
|---|---|---|---|
| Age at time of test (y) | Males | Females | Total |
| 21-29 | 12 | 8 | 10 |
| 30-29 | 4 | 16 | 10 |
| 40-49 | 40 | 28 | 34 |
| 50-59 | 20 | 24 | 22 |
| 60-69 | 20 | 28 | 24 |
| 70-79 | 12 | 32 | 22 |

Includes both solid tissue and blood cell cancers.

The overall incidence of positive test was 10% in the 21 to 29 year age group and stabilized at about 22% between 50 and 79 years. The marked increase in positive ONCOblots in the 40 to 49 year old males was due to a disproportionate number of early prostate indications within this population, a number of which would likely never develop in overt disease. Otherwise, for all age groups, the observed incidence of cancer matched closely the incidences predicted from the National Cancer Institute Seer Cancer Statistics Review (Table 6) for between 10 and 20 years rather than the previous estimates of 7 to 10 years to be provided by the 2-D gel-western blot protocol lacking the NADH/functionalized linker modified version of the present invention consistent with the 2- to 3-fold increase in sensitivity of the test over that of the original test.

TABLE 6

Risk of being diagnosed with cancer for different age groups from the National Cancer Institute Seer Cancer Statistics Review (Howlander, N. et al. SEER Cancer Statistics Review, 1875-2912, *National Cancer Institute, Bethesda, MD*).

| Current Age | +10 years | +20 years | +30 years | Ever |
|---|---|---|---|---|
| 20 | 0.46 | 1.52 | 4.13 | 40.73 |
| 30 | 1.08 | 3.72 | 9.64 | 40.77 |
| 40 | 2.70 | 8.75 | 19.44 | 40.55 |
| 60 | 13.47 | 26.28 | 34.95 | 37.10 |
| 70 | 17.16 | 27.91 | — | 30.61 |
| 80 | 16.15 | — | — | 20.40 |

The findings show that the 2-D gel-western blot test as described in the present invention has the potential to detect cancer earlier than any test previously reported. Certainly, not all of the early detected cancers would be expected to develop into clinically diagnosed disease but, based on the comparisons provided, in the order of 50% would have a high probability of so doing. At least with prostate cancer, positive ONCOblot results have been recorded for subjects with PSA values as low as 0.5 ng/ml in the age group of 40 to 49 year old males as one explanation for the exceptionally high incidence of cancer indicated by the functionalized ONCOblot test.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for detecting one or more ENOX2 variants from a subject, comprising the steps of:
   collecting a sample from the subject prior to electrophoretic protein separation;
   activating electrophoretically separated ENOX2 transcript variants with an ENOX2 electron donor; and
   detecting the presence of the one or more activated ENOX2 transcript variants using a pan-ENOX2 detectable binding reagent, wherein the presence of one or more activated ENOX2 transcript variants in the sample, whereby a 10 to 100 fold increase in detection sensitivity is obtained for the one or more activated ENOX2 transcript variants when compared to an equivalent non-activated ENOX2 transcript variant.

2. The method of claim 1, wherein the ENOX2 electron donor required to activate the ENOX2 transcript variants is selected from at least one of a reduced pyridine nucleotide, NADH, NAD(P)H, or a synthetic substrate that is an ENOX2 electron donor, and detecting the one or more activated ENOX2 transcript variants on the 2D blot, wherein the final concentration of NADH or NAD(P)H is in the range 10 µM to 50 µM.

3. The method of claim 1, further comprises performing two dimensional (2D) electrophoretic protein separation and blotting onto a film or paper.

4. The method of claim 1, wherein the pan-ENOX2 detectable binding reagent comprises SEQ ID NO:11.

5. The method of claim 1, wherein the sample is a blood, serum, plasma, urine, cerebrospinal fluid or a body fluid.

6. The method of claim 1, wherein the pan-ENOX2 detectable binding reagent comprises an anti-ENOX2 scFv fusion protein that is:
   non-aggregating at between 4° C. and 40° C.;
   comprises a small side chain (Gly/Ser) of amino acid residues containing two cysteines (C) spaced as either CXXXXC or CXXXXXC; and
   is capable of forming an interchain disulfide bond with the protein disulfide-thiol interchange functional motif of ENOX2.

7. The method of claim 4, further comprising storing the pan-ENOX2 detectable binding reagent comprises an scFv of SEQ ID NO:1 in 50% glycerol to prevent aggregation, wherein the stability, binding efficiency, and shelf life of the scFv of SEQ ID NO:11 is improved.

8. The method of claim 1, further comprising concentrating the one or more ENOX2 transcript variants in the sample, wherein the sample is a blood, serum, or plasma sample, on a nickel-agarose substrate that binds the one or more ENOX2 transcript variants.

9. The method of claim 1, further comprises detecting the one or more ENOX2 variants and/or determining a tissue of origin of the one or more ENOX2 variants at least one year in advance of clinical symptoms.

10. The method of claim 1, further comprises determining a tissue of origin of one or more cancers of unknown primary (CUP).

11. The method of claim 1, further comprises screening for at least one of: early cancer in populations with family cancer histories, environmental exposures, or in a general population.

12. The method of claim 1, further comprises determining a tissue of origin of the one or more activated ENOX2 transcript variants based on the presence of breast cancer ENOX2 transcript variants.

13. The method of claim 1, further comprises resolving proteins at 53 and/or 79 to 85 kDa as total protein loading controls.

14. The method of claim 1, further comprises detecting stage 0 and stage 1 cancers and determining the tissue of origin of the cancer.

15. The method of claim 1, wherein an incidence of false positives and confirmed false negatives of the predicted cancer is less than 1%.

16. The method of claim 1, wherein the sensitivity of the method for detecting the cancer is greater than 97%.

17. The method of claim 1, further comprises monitoring the reemergence of the cancer, therein the presence of 2 million or less cancer cells is detectable based on the reemergence of the one or more activated ENOX2 transcript variants.

18. The method of claim 1, wherein the tissue of origin of the cancer detected is breast.

19. A method for determining the tissue of origin of an ENOX2 variant of breast cancer in a subject comprising:
   subjecting proteins in a sample from the subject to a two-dimensional (2D) molecular weight and isoelectric point electrophoretic protein separation;
   transferring the proteins to a protein capture film or paper;
   activating the electrophoretically separated ENOX2 transcript variants with an ENOX2 electron donor on the protein capture film or paper;
   detecting the activated ENOX2 transcript variants; and
   determining the tissue of origin of the ENOX2 variant based on the presence of one or more activated breast cancer ENOX2 transcript variants, wherein activation of the one or more ENOX2 transcript variants in situ increases the detection sensitivity by 10 to 100 fold when compared to non-activated ENOX2 transcript variants by identifying a location on the capture film or paper indicative of the presence of the one or more breast cancer ENOX2 transcript variants.

20. The method of claim 19, wherein the ENOX2 electron donor required to activate the ENOX2 transcript variants is selected from at least one of a reduced pyridine nucleotide, NADH, NAD(P)H, or a synthetic substrate that is an ENOX2 electron donor, and detecting the one or more activated ENOX2 transcript variants on the 2D blot, wherein the final concentration of NADH or NAD(P)H is in the range 10 µM to 50 µM.

21. The method of claim 19, further comprising the steps of performing two dimensional (2D) electrophoretic protein separation and blotting onto a film or paper, wherein the ENOX2 electron donor is selected from at least one of a reduced pyridine nucleotide, NADH, NAD(P)H, or a synthetic substrate that is an ENOX2 electron donor, and detecting the one or more activated ENOX2 transcript variants on the 2D blot, wherein the final concentration of NADH or NAD(P)H is in the range 10 µM to 50 µM.

22. The method of claim 19, wherein the pan-ENOX2 detectable binding reagent comprises SEQ ID NO:11.

23. The method of claim 19, wherein the sample is a blood, serum, plasma, urine, cerebrospinal fluid or a body fluid.

24. The method of claim 19, wherein the pan-ENOX2 detectable binding reagent comprises an anti-ENOX2 scFv fusion protein is:
   non-aggregating at between 4° C. and 40° C.:
   comprises a small side chain (Gly/Ser) amino acid residues containing two cysteines (C) spaced as either CXXXXC or CXXXXXC; and
   is capable of forming an interchain disulfide bond with the protein disulfide-thiol interchange functional motif of ENOX2.

25. The method of claim 19, wherein the pan-ENOX2 detectable binding reagent comprises an scFv of SEQ ID NO:11, wherein the stability, binding efficiency, and shelf life of the scFv of SEQ ID NO:1 is improved by storing in 50% glycerol to prevent aggregation.

26. The method of claim 19, wherein the step of concentrating the blood, serum, or plasma sample is defined further as concentrating the one or more ENOX2 transcript variants using a nickel-agarose substrate to bind and concentrate the one or more ENOX2 transcript variants.

27. The method of claim 19, further comprises detecting the cancer and/or determining a tissue of origin of a human breast cancer at least one year in advance of clinical symptoms.

28. A blot comprising one or more electrophoretically separated proteins from a concentrated sample from a subject, wherein the blot is exposed to a pan-ENOX2 detecting reagent and to a reducing substrate for ENOX2 that activates the ENOX2 transcript variants on the blot, wherein the blot is analyzed for the present of one or more activated breast cancer ENOX2 transcript variants, wherein the presence of the one or more activated ENOX2 transcript variants is used to detect and determine a tissue of origin of a human cancer at least one year in advance of clinical symptoms, and the activation of the one or more ENOX2 transcript variants in situ increases the detection sensitivity by 10 to 100 fold when compared to non-activated ENOX2 transcript variants.

* * * * *